(12) United States Patent
Tsuchiya et al.

(10) Patent No.: US 8,355,044 B2
(45) Date of Patent: Jan. 15, 2013

(54) RETICLE DEFECT INSPECTION APPARATUS AND RETICLE DEFECT INSPECTION METHOD

(75) Inventors: Hideo Tsuchiya, Tokyo (JP); Toshiyuki Watanabe, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 931 days.

(21) Appl. No.: 12/432,182

(22) Filed: Apr. 29, 2009

(65) Prior Publication Data

US 2009/0284591 A1  Nov. 19, 2009

(30) Foreign Application Priority Data

May 16, 2008 (JP) .................................. 2008-129163
Jan. 30, 2009 (JP) .................................. 2009-019905

(51) Int. Cl.
*H04N 9/47* (2006.01)
(52) U.S. Cl. ......................................... 348/92; 348/129
(58) Field of Classification Search .................. 382/141, 382/144; 348/92, 125, 126, 129
See application file for complete search history.

(56) References Cited

U.S. PATENT DOCUMENTS

| | | | | |
|---|---|---|---|---|
| 4,587,617 A | * | 5/1986 | Barker et al. | 382/149 |
| 4,641,353 A | * | 2/1987 | Kobayashi | 382/144 |
| 5,744,381 A | | 4/1998 | Tabata et al. | |
| 6,529,621 B1 | * | 3/2003 | Glasser et al. | 382/144 |
| 6,947,587 B1 | * | 9/2005 | Maeda et al. | 382/149 |
| 7,076,394 B2 | | 7/2006 | Ikeda | |
| 2009/0214102 A1 | * | 8/2009 | Maeda et al. | 382/144 |
| 2012/0086799 A1 | * | 4/2012 | Hess | 348/125 |

FOREIGN PATENT DOCUMENTS

| | | |
|---|---|---|
| JP | 8-247738 | 9/1996 |
| JP | 2004-271444 | 9/2004 |

\* cited by examiner

*Primary Examiner* — Aaron Strange
(74) *Attorney, Agent, or Firm* — Oblon, Spivak, McClelland, Maier & Neustadt, L.L.P.

(57) ABSTRACT

The present invention provides a reticle defect inspection method and a reticle defect inspection apparatus capable of calibrating the offset and gain of a sensor amplifier using a product reticle even though black and white regions each sufficiently wider than a TDI sensor imaging area do not exist in the product reticle. An output of each pixel of the TDI sensor is amplified by the sensor amplifier. A bottom value of the amplified amount-of-light signal of each pixel is stored by bottom value storing means of offset/gain calibrating means, and a peak value thereof is stored by peak value storing means. The offset of each pixel is calculated by offset calculating means based on the bottom value of each pixel. The gain of each pixel is calculated by gain calculating means based on the offset of each pixel and the peak value of each pixel. The calculated offset and gain of each pixel are stored in a register and thereby the offset and gain of the sensor amplifier are calibrated.

9 Claims, 15 Drawing Sheets

RETICLE DEFECT INSPECTION APPARATUS AND RETICLE DEFECT INSPECTION METHOD

BACKGROUND OF THE INVENTION

1. Field of the Invention

The present invention relates to a reticle defect inspection apparatus and a reticle defect inspection method. The present invention relates particularly to a calibration for an offset and gain of sensor amplifier means that normalizes a TDI sensor output.

2. Background Art

In order to form patterns on a substrate (called also "wafer") in a semiconductor manufacturing process, the patterns are exposure-transferred onto the wafer by a scale-down projection exposure apparatus so-called "stepper" using an original drawing pattern (called also "reticle or mask" and hereinafter generically called "reticle") formed with circuit patterns. The reticle has patterns are normally formed on a light-transmitted glass substrate by a light-shielding material. Chromium (Cr) has been widely used as the light-shielding material. As a phase shift mask corresponding to one super-resolution technique, a halftone type phase shift mask in which a semi-transparent film comprised of molybdenum silicide (MoSi) or the like is formed as a light-shielding film, and a Levenson type phase shift mask to which a phase shift effect is imparted by changing the thickness of a glass substrate, are trying to be used. A pattern writing apparatus using an electron beam, capable of writing each micro circuit pattern is used in the manufacture of such a mask. When a pattern defect exists in the reticle, the defect is transferred onto the wafer. It is therefore necessary to perform a reticle defect inspection.

As reticle defect inspection methods, there are known a Die-to-Die inspection method and a Die-to-Database inspection method. The Die-to-Die inspection method is a method for comparing optical images of the same pattern located in different positions with each other. On the other hand, the Die-to-Database inspection method is a method for comparing a reference image generated from writing data (CAD data) used upon reticle fabrication and an optical image of a pattern of an actual reticle.

In order to generate the optical image, a charge storage type TDI (Time Delay Integration) sensor and a sensor amplifier for amplifying the output of the TDI sensor are used (refer to, for example, Japanese Patent Application Laid-Open No. 2004-271444). Since the contrast between the light-shielding film and the glass substrate is obtained to some extent in the halftone type phase shift mask in the case of an inspection by transmitted light, a technique to recognize a mask pattern with a light intensity signal of a sensor image light-received by a detection optical system in a manner similar to a chromium mask thereby to perform a defect decision can be adopted. There is a case in which the utilization of reflected light on a mask surface makes it easy to obtain contrast depending on the shape of a defect. There is also known an inspection apparatus equipped with a reflection inspection optical system in applications such as a particle inspecting function, etc.

It is known that a calibration for the offset and gain of the sensor amplifier is performed prior to the above comparison between the reference image and the optical image (refer to, for example, Japanese Patent No. 3410847). According to the Japanese Patent No. 3410847, a black region (light-shielding film region or halftone film region) having an area sufficiently broader than an imaging area of a TDI sensor for imaging transmitted light is imaged upon inspection by the transmitted light to calibrate the offset. Thereafter, a white region (glass substrate) having an area sufficiently wider than the imaging area of the TDI sensor is imaged to calibrate the gain. Upon inspection by reflected light, each part in which a chromium or halftone film exists becomes a white region by its reflection, and part of the glass substrate becomes a black region because no reflected light exists therein.

However, miniaturization of each pattern written on a product reticle has been advanced in recent years, and a black region or a white region having a sufficiently wide area might not exist in a product pattern itself. It has also been partly practised to prepare a black or white region having a sufficiently wide area other than each product pattern for calibration. However, the occupied area of the product pattern has been enlarged, and the pattern for the calibration becomes a matter of being not necessarily prepared. In this case, an offset/gain calibration reticle (hereinafter called "calibration reticle") in which black and white regions of the same kind of film as the product reticle are formed has been used. After the offset and gain of the sensor amplifier have been calibrated using the calibration reticle, it is replaced with the corresponding product reticle to execute a defect inspection. Such a reticle replacement incurs a reduction in throughput and causes a risk that errors will be contained in the amplitude of a sensor signal and the offset due to an error in finished accuracy of a light-shielding film between the calibration reticle and the product reticle.

When the thickness of the glass substrate differs, transmittance of light varies. Therefore, there is a possibility that the offset and gain of the senor amplifier both optimally adjusted or calibrated using the calibration reticle will not be rendered optimal in the product reticle.

Due to the reasons mentioned above, it is desirable to calibrate the offset and gain of the sensor amplifier using the product reticle itself corresponding to the reticle to be inspected, without using the calibration reticle.

SUMMARY OF THE INVENTION

With the foregoing in view, the present invention aims to provide a reticle defect inspection method and a reticle defect inspection apparatus capable of calibrating the offset and gain of a sensor amplifier using a product reticle even though black and white regions each sufficiently wider than a TDI sensor imaging area do not exist in the product reticle.

According to one aspect of the present invention, in the reticle defect inspection method, an image sensor is moved relative to a reticle, and an optical image obtained by amplifying an output of each pixel of the image sensor by a sensor amplifier is compared with a reference image defined as a standard image relative to the optical image to perform a defect inspection of the reticle. The sensor amplifier is capable of calibrating a gain and an offset of a signal amplitude every pixel. Before the defect inspection, some of patterns of the reticle are imaged by the image senor, and bottom and peak values of an amount-of-light signal of each pixel amplified by the sensor amplifier are stored. Then, a plurality of offsets are set in the sensor amplifier by setting each offset of the signal amplitude for each pixel of the sensor amplifier, based on stored bottom value of each pixel. Then, a plurality of gains are set in the sensor amplifier by setting each gain of signal amplitude for each pixel of the sensor amplifier, based on the offset of the signal amplitude of each pixel and on stored peak value of each pixel.

According to another aspect of the present invention, the reticle defect inspection apparatus comprises a light irradiating mechanism for irradiating a reticle formed with each pattern with light and driving means for driving a stage which holds the reticle thereon. An image sensor detects amount-of-light signal of light transmitted through or reflected from the reticle at a plurality of pixels. A sensor amplifier amplifies an output of each pixel of the image sensor every pixel and generates an optical image. The sensor amplifier is capable of calibrating a gain and an offset of a signal amplitude every pixel. Reference image generating means generate a reference image defined as a standard image relative to the optical image. Detecting means compare the optical image with the reference image thereby to detect a defect of each pattern of the reticle. Storing means, when the stage is driven by the driving means before the inspection by the detecting means to image some of the patterns by the image sensor, store bottom and peak values of an amount-of-light signal of each pixel amplified by the sensor amplifier. Offset setting means set an offset of a signal amplitude for each pixel of the sensor amplifier, based on the bottom value of each pixel stored by the storing means. Gain setting means set a gain of a signal amplitude for each pixel of the sensor amplifier, based on the offset of the signal amplitude for each pixel and the peak value of each pixel stored by the storing means.

Another object and an advantage of the present invention are apparent from the following description.

DETAILED DESCRIPTION OF THE EMBODIMENTS

Figure 1:
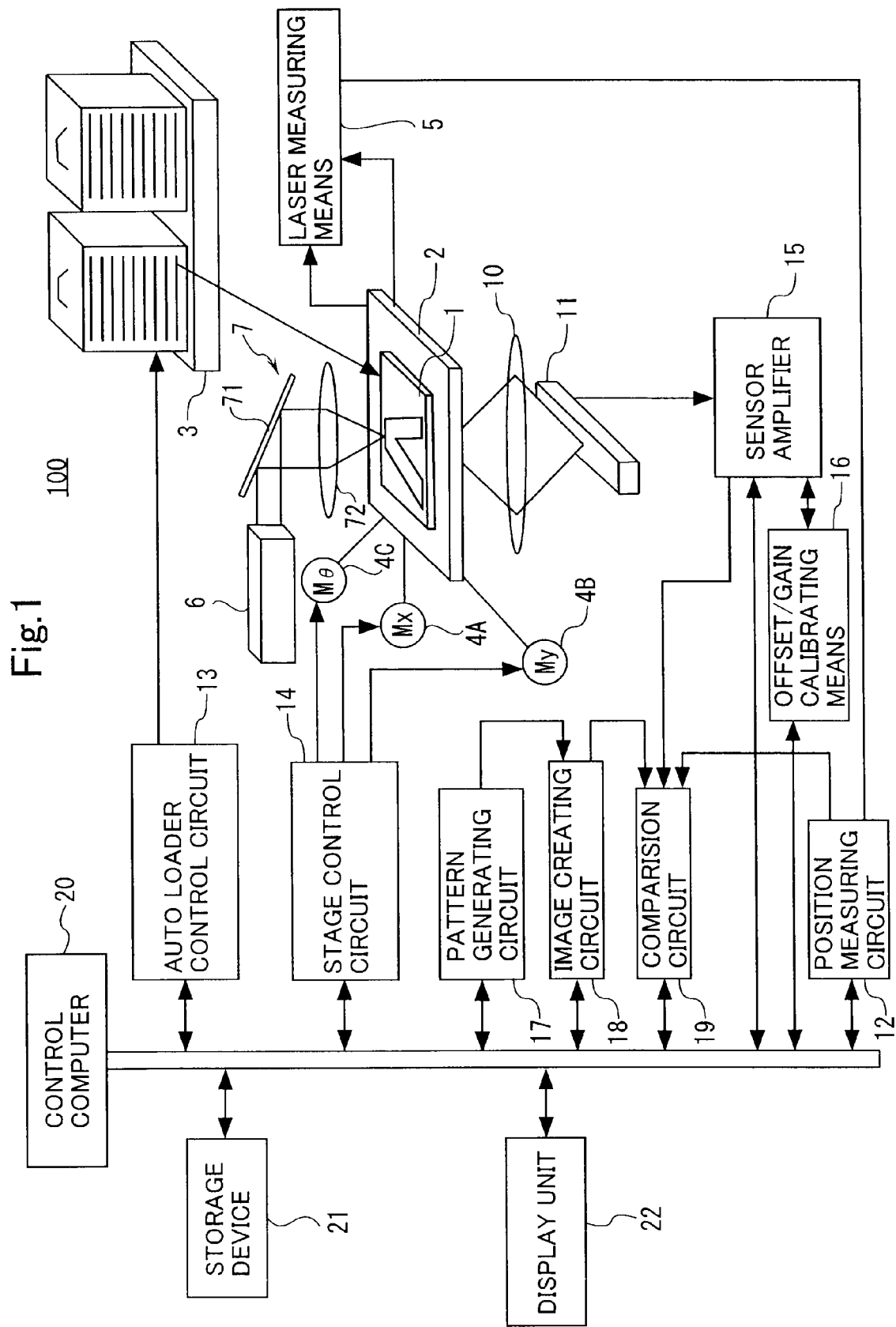
FIG. 1 is a diagram showing a schematic configuration of a reticle defect inspection apparatus 100 according to a first embodiment of the present invention.
Figure 2:
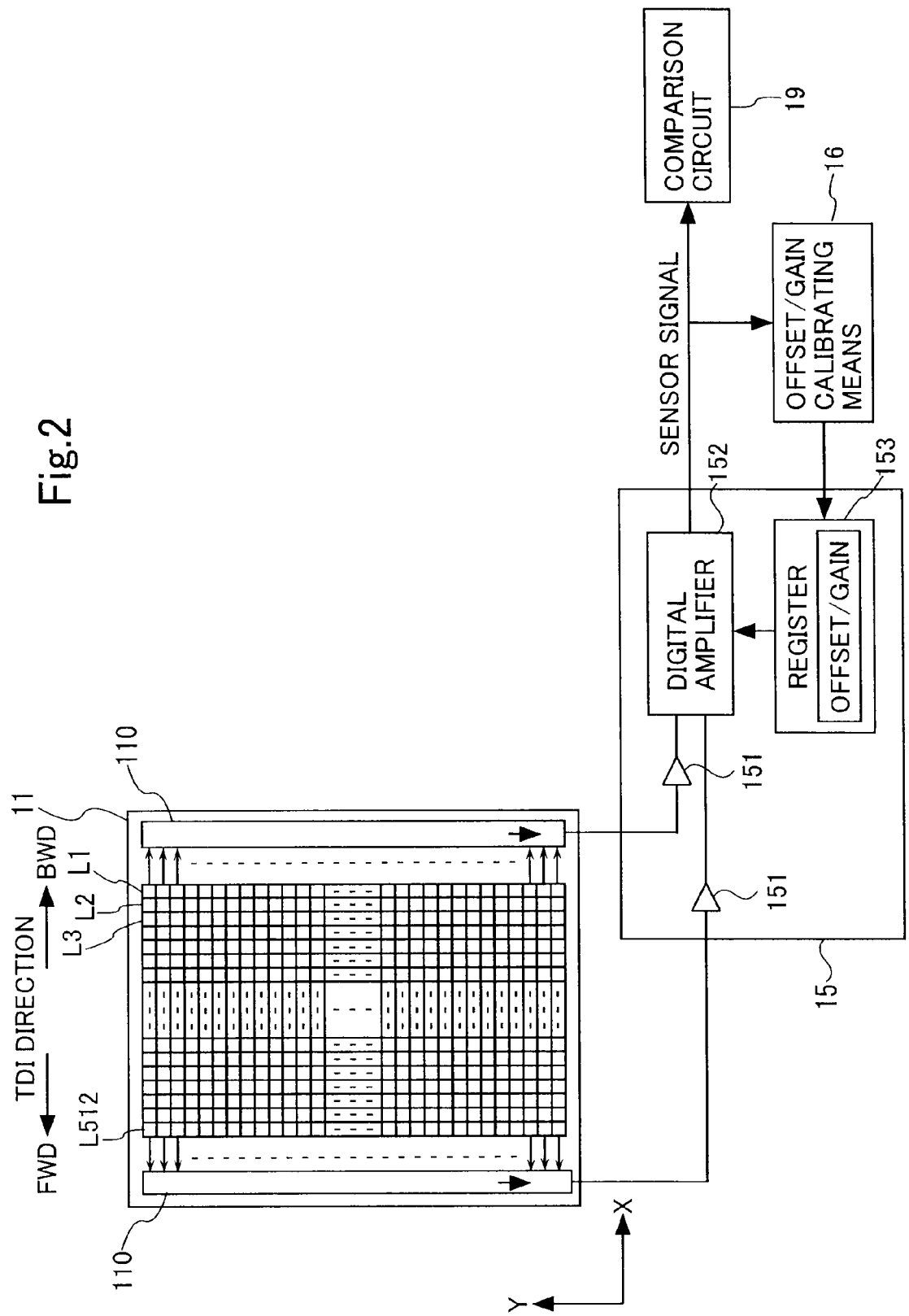
FIG. 2 is a schematic diagram illustrating configurations of a TDI sensor 11 and a sensor amplifier 15 shown in FIG. 1.
Figure 3:
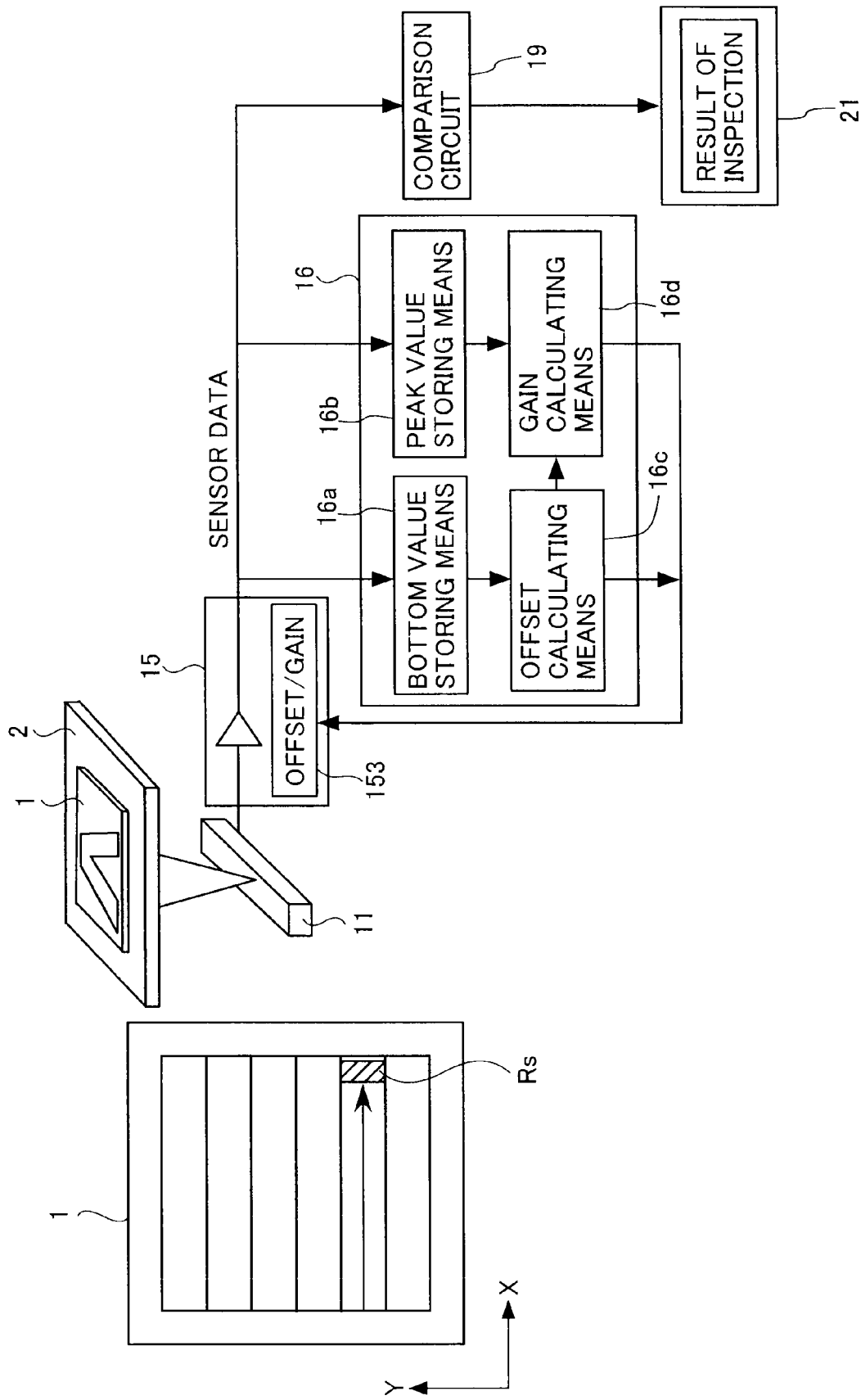
FIG. 3 is a schematic diagram depicting a configuration of offset/gain calibrating means 16 shown in FIG. 1.

The embodiments of the present invention will hereinafter be described with reference to the accompanying drawings.
First Embodiment FIG. 1 is a schematic diagram showing a configuration of a reticle defect inspection apparatus 100 according to a first embodiment of the present invention. FIG. 2 is a schematic diagram showing configurations of a TDI sensor 11 and a sensor amplifier 15 shown in FIG. 1. FIG. 3 is a schematic diagram showing a configuration of offset/gain calibrating means 16 shown in FIG. 1.

The reticle defect inspection apparatus 100 shown in FIG. 1 has a stage 2 that holds a reticle 1 to be inspected. The reticle 1 is conveyed onto the stage 2 from an auto loader 3. The auto loader 3 is controlled by an auto loader control circuit 13.

The stage 2 is driven in X, Y and $\theta$ directions by an X-direction motor 4A, a Y-direction motor 4B and a $\theta$-direction (a reticle plate rotation direction) motor 4C respectively. Drive control of these motors 4A, 4B and 4C are executed by a stage control circuit 14. The position in the X and Y directions, of the stage 2 is detected by, for example, laser measuring means 5 such as a laser interferometer and a position measuring circuit 12 connected to the laser measuring means 5. The process of imaging the reticle intended for inspection by a sensor while being continuously moved at a constant speed in the X direction, for example, moving the reticle in the Y direction at a stripe end and thereafter imaging the same by the sensor while it is continuously moved at a constant speed in the direction opposite to the X direction is repeated to image the entire inspection region of the reticle.

The reticle defect inspection apparatus 100 includes a light source 6 which emits laser light, and a transmission-illumination optical system 7 which irradiates the reticle 1 with the laser light emitted from the light source 6. The transmission-illumination optical system 7 has a mirror 71 and a condenser lens 72.

The reticle defect inspection apparatus 100 has an objective lens 10 which collects light transmitted through the reticle 1 to provide an image on the TDI (Time Delay Integration) sensor 11.

The TDI sensor 11 corresponding to an image sensor is of a two-dimensional CCD sensor as shown in FIG. 2, which has, for example, a rectangular imaging or scanning region Rs of 2048 pixels×512 pixels (144 μm×36 μm where one pixel is 70 nm×70 nm). Namely, the TDI sensor 11 comprises a plurality of stages (512 stages, for example) of lines L1, L2, . . . , L512 in a TDI direction. Each of the lines L is formed by a plurality of pixels (2048 pixels, for example). The TDI sensor 11 is provided in such a manner that the TDI direction (512-stage direction) of the TDI sensor 11 coincides with the X direction of the stage 2. The stage 2 is moved to thereby move the TDI sensor 11 relative to the reticle 1, whereby a pattern of the reticle 1 is obtained or imaged by the TDI sensor 11. When the TDI sensor 11 is moved relatively in the right or backward direction in FIG. 2, the left or forward direction (FWD) in FIG. 2 is brought to a charge storage direction (TDI direction) of the TDI sensor 11. In this case, electrical charges are stored while being sequentially transferred from the line L1 corresponding to a first stage to the lines L2, L3, . . . in the FWD direction, and an image signal corresponding to one line (2048 pixels) is outputted from the line L512 corresponding to a final stage.

When the moving direction of the stage 2 is reversed, i.e., the TDI sensor 11 is moved relatively in the left or forward direction in FIG. 2, the charge storage direction of the TDI sensor 11 is switched to the backward direction (BWD) in FIG. 2. The TDI sensor 11 has output parts 110 at both ends thereof as viewed in the charge storage direction. That is, the TDI sensor 11 is configured so as to be capable of reading the electrical charges from a bi-direction.

The TDI sensor 11 is connected to the sensor amplifier 15. The sensor amplifier 15 brings amount-of-light signals of each pixel inputted from the TDI sensor 11 to calibration and outputs the same to a comparator or comparison circuit 19. As shown in FIG. 2, the sensor amplifier 15 is equipped with an analog amplifier 151 which amplifies the signal of each pixel at a fixed magnification, and a digital amplifier 152 which amplifies the signal of each pixel with an offset and gain stored in a register 153. The offset and gain for each pixel stored in the register 153 are adjusted or calibrated by the offset/gain calibrating means 16 to be described later (refer to FIG. 3).

Incidentally, while the TDI sensor 11 is used as the image sensor in the present embodiment, other image sensors such as a line sensor and an area sensor can be used instead of the TDI sensor 11.

The reticle defect inspection apparatus 100 includes a pattern generating circuit 17 and a reference image creating circuit 18 for generating a reference image defined as a comparison reference for each optical image. The pattern generating circuit 17 develops CAD data (drawing data) or the like stored in a storage device 21 and outputs the developed data to the reference image creating circuit 18. The reference image creating circuit 18 collectively performs a resize process, a corner round-off process and a point spread functions (PSF) filter process on the developed data inputted from the pattern generating circuit 17 thereby to generate a reference image and outputs the same to the comparison circuit 19. The storage device 21 is of, for example, a magnetic disk device, a magnetic tape device, FD or a semiconductor memory or the like.

The comparison circuit 19 compares the optical image inputted from the sensor amplifier 15 with the reference image inputted from the reference image creating circuit 18 and detects the result of comparison as a pattern form defect where both pattern forms differ from each other. The result of inspection by the comparison circuit 19 is stored in the storage device 21. Thus, an operator is able to read the result of inspection from the storage device 21 and display it on a display unit 22 such as a display thereby to confirm it.

The reticle defect inspection apparatus 100 has the control computer 20 which executes overall control such as a calibration for the offset/gain of the sensor amplifier 15, alignment of the stage 2, etc. in addition to a normal pattern defect inspection. The above-mentioned position measuring circuit 12, auto loader control circuit 13, stage control circuit 14, sensor amplifier 15, offset/gain calibrating means 16, pattern generating circuit 17, reference image creating circuit 18, comparison circuit 19, storage device 21 and display unit 22, etc. are connected to the control computer 20.

As described above, the outputs of the respective pixels of the TDI sensor 11 are amplified every pixel by the sensor amplifier 15 to generate the optical image. There is a need to generate the optical image with satisfactory accuracy in order to perform a defect inspection at the comparison circuit 19 with satisfactory accuracy. That is, it is necessary to make use of the dynamic range of the sensor amplifier 15 efficiently.

Figure 4:
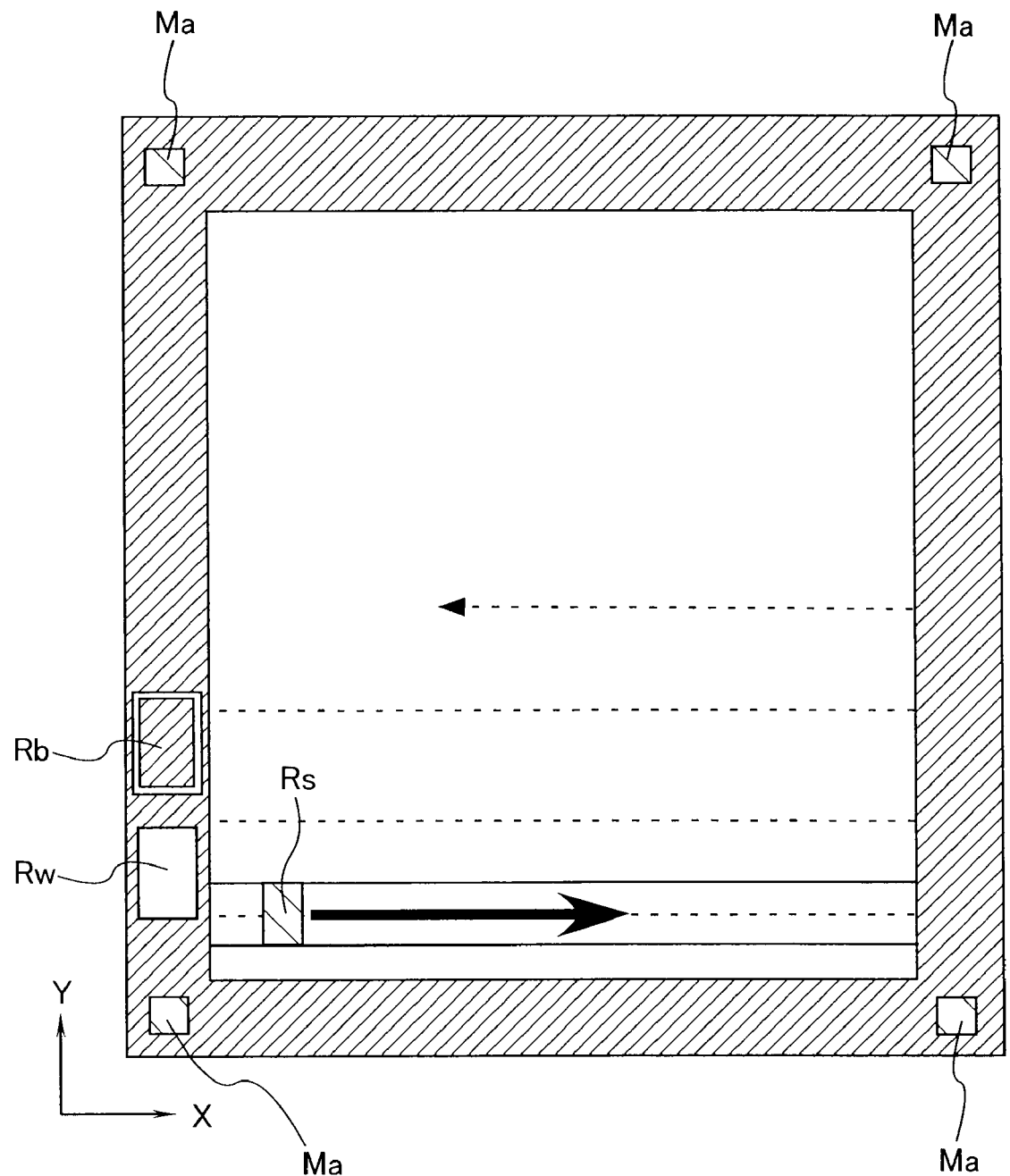
FIG. 4 is a conceptual diagram showing a black region Rb and a white region Rw formed in a conventional product reticle.

The calibration for the offset/gain of the sensor amplifier 15 has heretofore been carried out before the defect inspection. Conventionally, relatively large all white and all black regions exist in a product pattern itself. The above calibration could be done by selecting a spot sufficiently wider than the imaging region of the TDI sensor. Even though the large white and black betta regions are not provided in the product pattern itself, alignment patterns for a transfer apparatus, and a black region Rb and a white region Rw each having an area sufficiently wider than the imaging region Rs of the TDI sensor as partly shown in FIG. 4 have been formed in a non-inspected region of a product reticle for the calibration of the inspection apparatus. FIG. 4 is conceptual diagram showing a black region Rb and a white region Rw formed in a conventional product reticle. Conventionally, the TDI sensor has been made stationary to the wide region like the black region Rb to set the offset of signal amplitude of the sensor amplifier, based on the result of imaging. Further, the TDI sensor has been made stationary to the wide region like the white region Rw to set the gain of the signal amplitude of the sensor amplifier, based on the result of imaging.

However, the miniaturization of each pattern written on a reticle has been advanced recently. It is often the case that the black and white regions each having the sufficiently wide area are not formed in the product reticle. It has also been partly practised to prepare a black or white region having a sufficiently wide area, other than each product pattern for calibration as in the case of Rb and Rw described above. However, each pattern to be included or held in the product reticle has been enlarged or spread, thus leading to the situation that each pattern for calibration is not necessarily prepared. Therefore, the offset and gain of the sensor amplifier are calibrated using the reticle for offset/gain calibration and thereafter the reticle has been replaced with the product reticle. The replacement of such a reticle may cause a reduction in throughput. Further, since the transmittance varies depending on the thickness of a glass substrate of the reticle, the offset and gain of the sensor amplifier, which have been calibrated using the calibration reticle, have a possibility of being not optimal for the product reticle. Doing so results in degradation of the accuracy of a defect inspection. Thus, even when the black and white regions each having the sufficiently wide area are not formed in the product reticle, it is desirable to calibrate the offset and gain of the sensor amplifier using the product reticle.

Thus, in the first embodiment, the offset/gain calibrating means 16 for calibrating the offset and gain of the sensor amplifier 15 is provided as shown in FIG. 3. As shown in FIG. 3, the offset/gain calibrating means 16 is equipped with bottom value storing means 16a, peak value storing means 16b, offset calculating means 16c and gain calculating means 16d.

The bottom value storing means 16a, peak value storing means 16b, offset calculating means 16c and gain calculating means 16d are respectively provided every plural pixels that constitute one line of the TDI sensor 11. That is, the means 16a through 16d are provided every 2048 where comprised of 2048 pixels corresponding to one line of the TDI sensor 11.

The bottom value storing means 16a stores or holds therein a bottom value of the amount-of-light signal of each pixel, which has been amplified by the sensor amplifier 15. The peak value storing means 16b stores or holds a peak value of the amount-of-light signal of each pixel. The offset value calculating means 16c calculates an offset of each pixel of the sensor amplifier 15, based on the bottom value of each pixel stored in the bottom value storing means 16a. The gain calculating means 16d calculates the gain of each pixel of the sensor amplifier 15, based on the offset of each pixel calculated by the offset calculating means 16c and the peak value of each pixel held in the peak value storing means 16b.

Figure 5:
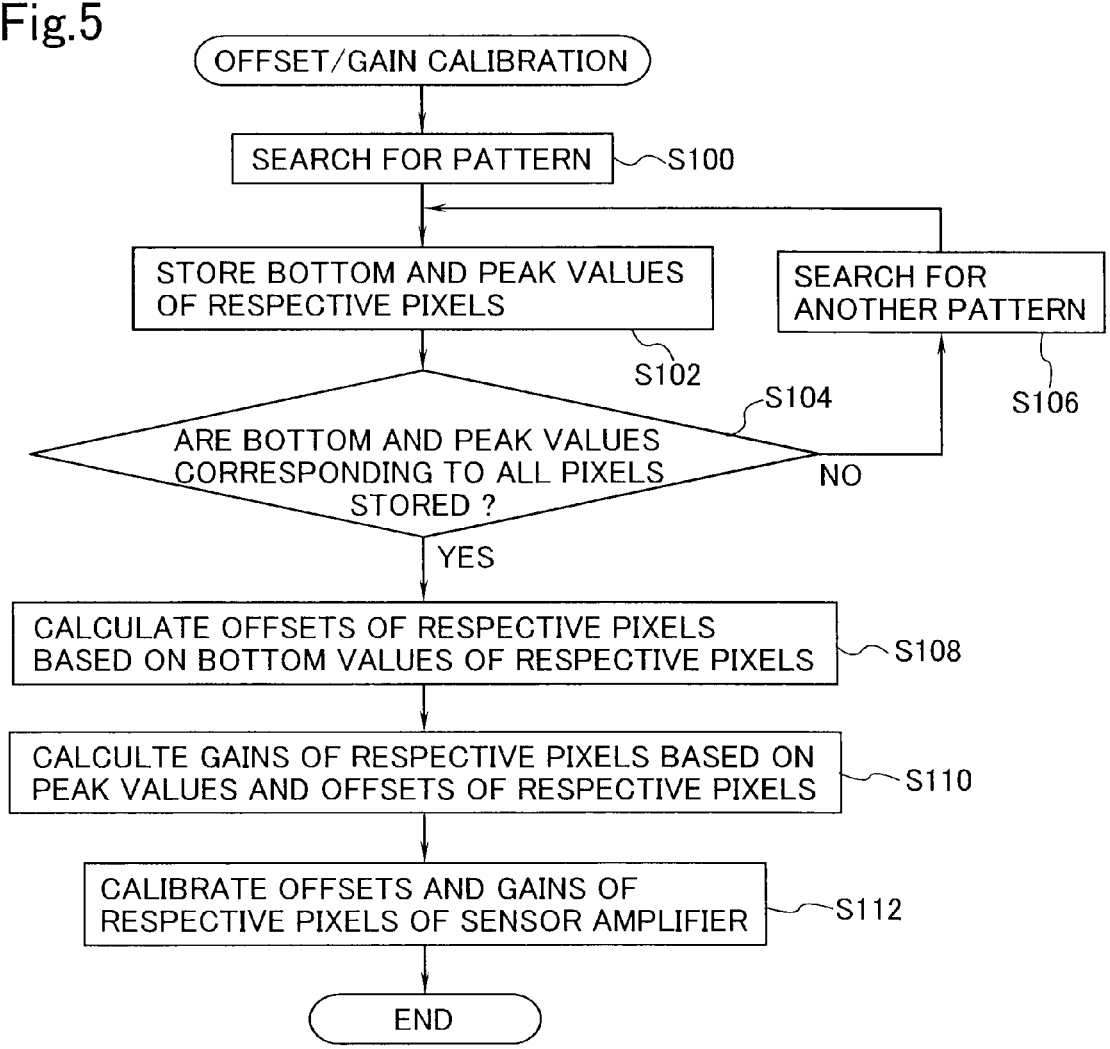
FIG. 5 is a flowchart showing an offset/gain calibration control routine mainly executed by a control computer 20 and the offset/gain calibrating means 16 in the first embodiment.

Concrete control will be explained below with reference to FIG. 5. FIG. 5 is a flowchart showing an offset/gain calibration control routine mainly executed by the control computer 20 and the offset/gain calibrating means 16 in the first embodiment. The routine shown in FIG. 5 is started up before the pattern defect inspection.

Figure 6:
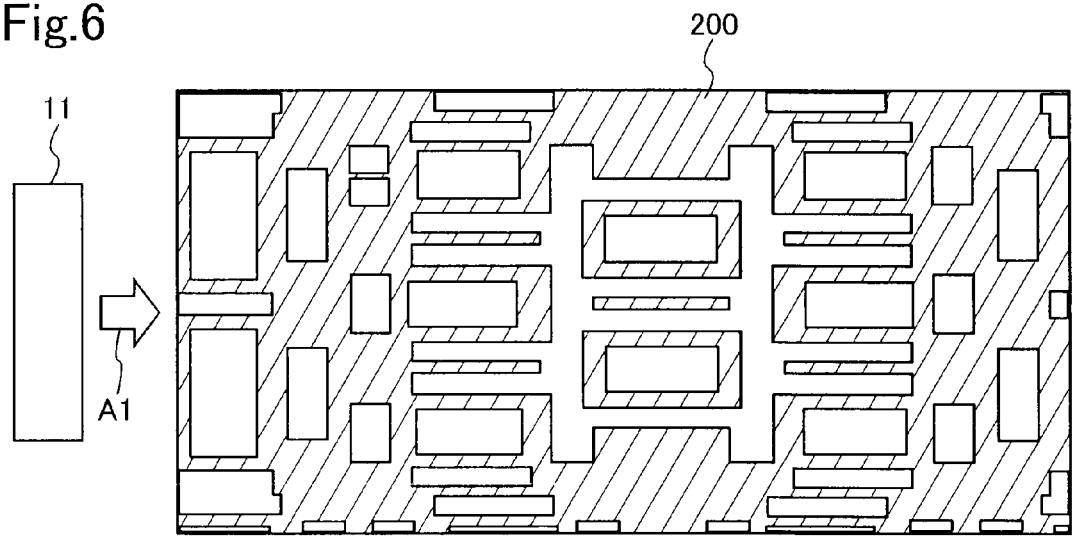
FIG. 6 is a diagram illustrating patterns to be searched in accordance with the routine shown in FIG. 5.

According to the routine shown in FIG. 5, the search of a pattern to be imaged by the TDI sensor 11 is first executed (Step S100). At this Step S100, such a pattern that each pixel of the TDI sensor 11 reaches all white and black patterns at least once, e.g., such a pattern 200 as shown in FIG. 6 is searched. A part hatched within the pattern 200 indicates a black pattern comprised of a light shielding film (chromium film). White parts in the pattern 200 indicate white patterns each comprised of a glass substrate. The pattern 200 is imaged by the TDI sensor 11 moved relatively in the direction indicated by arrow A1.

The pattern searching method at Step S100 referred to above is capable of, where design data or writing data of a reticle to be inspected is being inputted in the inspection apparatus or held in the storage device 21 as a database for database inspection, retrieving or searching for the data at the control computer 20 and thereby selecting a suitable pattern region (pre-scan region). Alternatively, a region to be pre-scanned can be determined by the way to decide the position of a region to be inspected in the neighborhood of its center, the position of an inspection range, which is brought closer to the inside thereof by 10% from its end, even without searching for or scanning the above data. Discrimination as to whether the offset and gain of each pixel are suitable is enabled practically by imaging that region.

Next, when the stage 2 is driven using the motors 4A and 4B and the pattern searched at Step S100 is scanned by the TDI sensor 11, the output of each pixel of the TDI sensor 11 is amplified by the sensor amplifier 15. At this time, the offset and gain of each pixel stored in the register 153 are used for signal amplification. The bottom values and peak values of the pixels outputted from the sensor amplifier 15 are stored by the offset/gain calibrating means 16 (Step S102). At this Step S102, the bottom values of the respective pixels are stored by the bottom value storing means 16a for the respective pixels, and the peak values of the respective pixels are stored by the peak value storing means 16b for the respective pixels.

The pattern (pattern corresponding to one stripe, for example) searched at Step S100 referred above is scanned by the TDI sensor 11. Thereafter, it is discriminated whether the bottom values and the peak values corresponding to all pixels (2048 pixels) have been stored (Step S104). It is discriminated at this Step S104 whether the bottom values and peak values of all pixels held at Step S102 respectively fall within a reference range (10%, for example). When it is discriminated at Step S104 that the bottom values and peak values corresponding to all pixels are not stored, a pattern (pattern corresponding to another one stripe, for example) different from the pattern searched at Step S100 is searched (Step S106). Thereafter, the other pattern searched at Step S106 is scanned by the TDI sensor 11 and the process of Step S102 is executed again.

When it is discriminated at Step S104 that the bottom values and peak values corresponding to all pixels have been stored, the offset calculating means 16c calculates the offset of each pixel, based on the bottom value of each pixel (Step S108). Thereafter, the gain calculating means 16d calculates the gain of each pixel, based on the peak value of each pixel and the offset of each pixel calculated at Step S108 (Step S110).

Thereafter, the offset and gain of each pixel of the sensor amplifier 15 are calibrated (set) based on the offset of each pixel calculated at Step S108 and the gain of each pixel calculated at Step S110 (Step S112). At Step S112, the offset and gain of each pixel outputted from the offset calculating means 16c and the gain calculating means 16d are inputted to the sensor amplifier 15. The inputted offset and gain of each pixel are stored in the register 153 thereby to calibrate (set) the offset and gain of each pixel. Thereafter, the present routine is finished. In doing so, the pattern defect inspection is executed.

In the first embodiment as described above, each pattern is scanned by the TDI sensor 11 before the pattern defect inspection, and the bottom value and peak value of each pixel of the output signal amplified by the sensor amplifier 15 are stored. Then, the offset of each pixel is calculated based on the stored bottom value of each pixel. The gain of each pixel is calculated based on the calculated offset of each pixel and the stored peak value of each pixel. Thereafter, the offset and gain of each pixel of the sensor amplifier 15 are calibrated (set) based on the calculated offset and gain of each pixel. Consequentially, the offset and gain of each pixel of the sensor amplifier can be calibrated using the product reticle in which the black and white regions each not having the area sufficiently wider than the imaging area of the TDI sensor exist. Thus, since the signal amplitude of the TDI sensor 11 is subjected to normalization matched with the actual product reticle to be inspected, an S/N ratio can be improved as compared with the use of another calibration reticle.

The reticle has a main chip region formed with a product pattern and a peripheral chip region formed with alignment marks other than the product pattern. There is a case in which the thickness of a light shielding film and the thickness of a transparent substrate are ununiform even within the surface of the main chip region. Even in such a case, the pattern of a main chip is scanned by the TDI sensor 11 and the signal amplitude of the TDI sensor 11 is normalized, thereby making it possible to perform practical and highly accurate normalization.

Second Embodiment

A second embodiment of the present invention will next be explained with reference to FIGS. 7 through 11.

Figure 7:
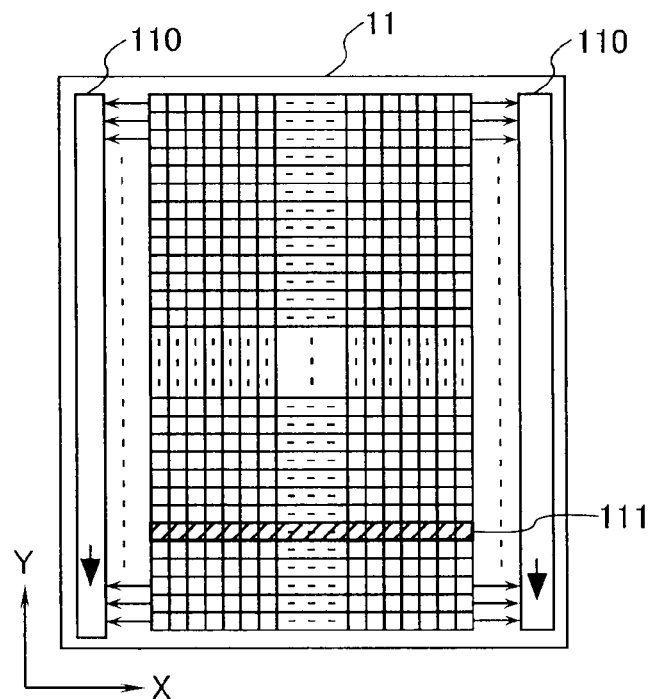
FIG. 7 is a diagram showing a TDI sensor 11.
Figure 8:
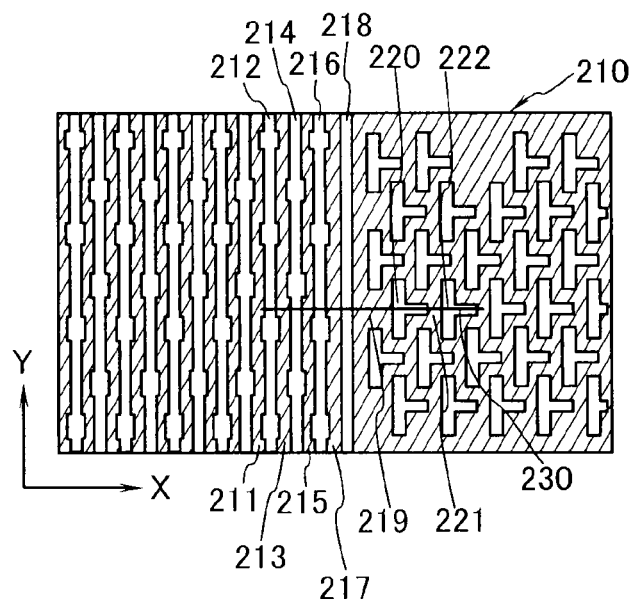
FIG. 8 is a diagram depicting an example of an image obtained (taken) where a stage moving speed and a TDI operation speed are synchronized.

It is considered that when the bottom values and peak values of the respective pixels are stored by the bottom value storing means 16a and the peak value storing means 16b, the moving speed of the stage 2 and the TDI operating speed in the TDI sensor 11 are normally synchronized. In such synchronization, an example of an image taken by a TDI sensor 11 shown in FIG. 7 is shown in FIG. 8. The image 210 shown in FIG. 8 is equivalent to one obtained by imaging reticle transmitted light by the TDI sensor 11. Thus, hatched parts in FIG. 8 correspond to light shielding portions, and white parts indicate light-transmitted portions respectively. A sensor output at each hatched part becomes a level close to a bottom value, whereas a sensor output at each white part becomes a level near a peak value.

Figure 9:
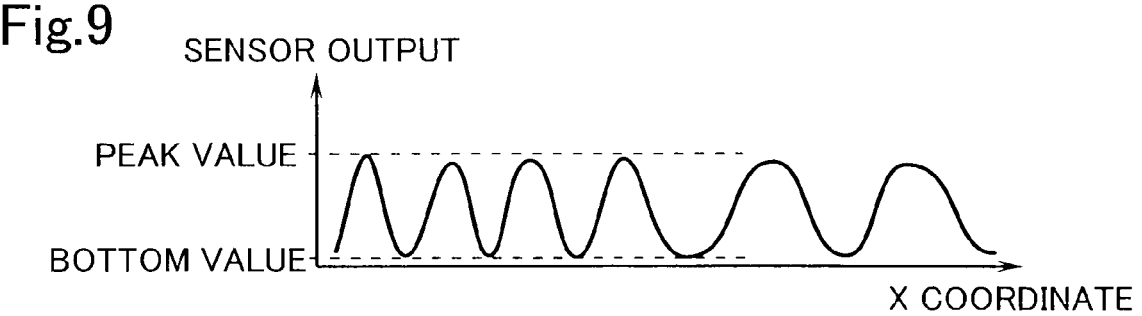
FIG. 9 is a diagram showing a TDI sensor output cut out along a straight line 230 shown in FIG. 8.

A sensor output cut out along a straight line 230 in FIG. 8 is shown in FIG. 9. This sensor output corresponds to the output of a pixel 111 hatched in FIG. 7. Since the left end of the straight line 230 shown in FIG. 8 is located in a hatched part (black line) 211, the sensor output shown in FIG. 9 is cut out from the neighborhood of the bottom value thereof. Thereafter, since the straight line 230 alternately cuts across thin white parts (thin white lines) 212, 214, 216 and 218 and thin hatched parts (thin black lines) 213, 215 and 217 as shown in FIG. 8, the thin peaks are obtained four times continuously as shown in FIG. 9. Thereafter, since the straight line 230 alternately cuts across a wide hatched part 219 and a wide white part 220 as shown in FIG. 8, a width-thick bottom and a width-thick peak are obtained as shown in FIG. 9.

Line widths of the thin white line patterns 212 and 214 across which the straight line 230 first cuts, and the interval therebetween are both 200 nm. As described above, the size of one pixel of the TDI sensor 11 is 70 nm×70 nm. Thus, there is a case in which when the micro pattern is imaged with respect to each sensor pixel, sufficient signal amplitude is not obtained if the position of each pattern that reaches the sensor pixel is not ideal.

Here, the amount of the reticle transmitted light is not brought to a uniform distribution, but to a Gaussian distribution with the maximum amount of light as the center under the influence of the optical system (image forming lens 10 or the like). Therefore, the position of the maximum amount of light is dispersed into two pixels depending on scan timing. Thus, when the pattern is imaged in a state in which the position of the maximum amount of light is being dispersed into the two pixels, the signal amplitude is reduced as compared with the case where the position of the maximum amount of light is located in the center of one pixel.

Figure 10:
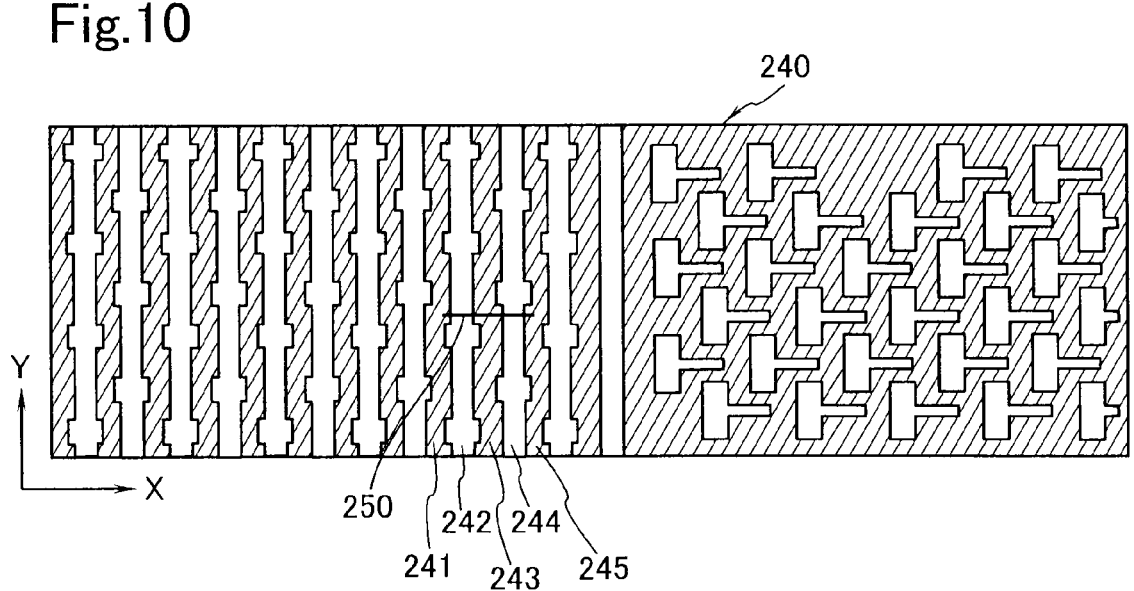
FIG. 10 is a diagram illustrating an example of an image taken where a stage moving speed is set slower than a TDI operation speed in a second embodiment of the present invention.
Figure 11:
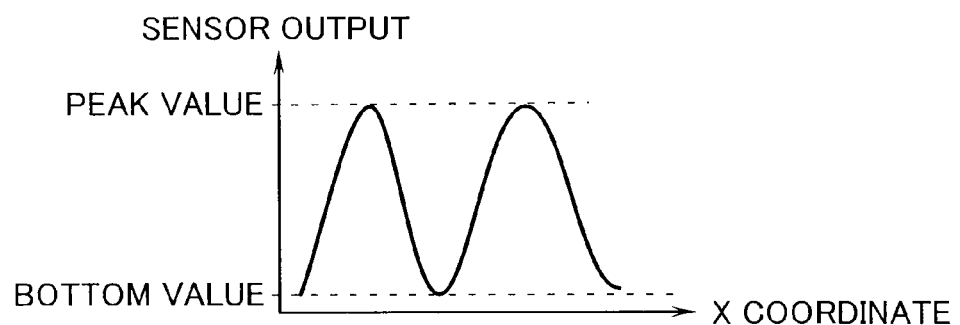
FIG. 11 is a diagram depicting a TDI sensor output cut out along a straight line 250 shown in FIG. 10.

Thus, in the second embodiment, the moving speed of the stage 2 is set slower than the TDI operating speed corresponding to the moving speed of each pixel in the TDI sensor 11 when the bottom and peak values are stored. The pixel moving speed depends on the size of each pixel and the imaging period. FIGS. 10 and 11 are respectively diagrams showing examples of an image and a sensor output where the stage moving speed is set slower than the TDI operating speed in the second embodiment. The image 240 shown in FIG. 10 is equivalent to one obtained by imaging reticle transmitted light by the TDI sensor 11 shown in FIG. 7 where the moving speed of the stage 2 is set to one-half the TDI operating speed. Thus, parts hatched in FIG. 10 correspond to light shielding portions, whereas white parts correspond to light-transmitted portions, respectively. A sensor output at each hatched part becomes a level near a bottom value, and a sensor output at each white part becomes a level close to a peak value.

The sensor output cut out along a straight line 250 shown in FIG. 10 is shown in FIG. 11. This sensor output corresponds to the output of the pixel 111 hatched in FIG. 7. Since a left end (cut-out start position) of the straight line 250 shown in FIG. 10 is the same position as the left end (cut-out start position) of the straight line 230 shown in FIG. 8, the sensor output shown in FIG. 11 is cut out from the same position as the sensor output shown in FIG. 9. That is, since the straight line 250 shown in FIG. 10 is cut out from a hatched part (black line) 241, the sensor output shown in FIG. 11 is cut out from the neighborhood of a bottom value thereof. Thereafter, since the straight line 250 alternately cuts across white parts (white lines) 242 and 244 and hatched parts (black lines) 243 and 245 as shown in FIG. 10, the peak can be obtained twice as shown in FIG. 11.

In the second embodiment, one narrow line is imaged so as to reach the plural pixels with the slowing down of the stage moving speed. Namely, an advantageous effect similar to oversampling is obtained. Therefore, each line width and interval in the image 240 shown in FIG. 10 become wider than those in the image 210 shown in FIG. 8. Thus, the opportunity of performing imaging when the position of the maximum amount of light is brought to the center of one pixel can be increased as compared with the case where the stage moving speed and the TDI operating speed are synchronized. With the execution of the imaging where the position of the maximum amount of light is brought to the pixel center, sufficient signal amplitude can be obtained as shown in FIG. 11. Thus, even when each micro pattern is imaged, the peak value of each pixel stored in the peak value storing means 16b can be enhanced sufficiently. It is therefore possible to make full use of the dynamic range of the sensor amplifier 15.

Third Embodiment

Figure 12:
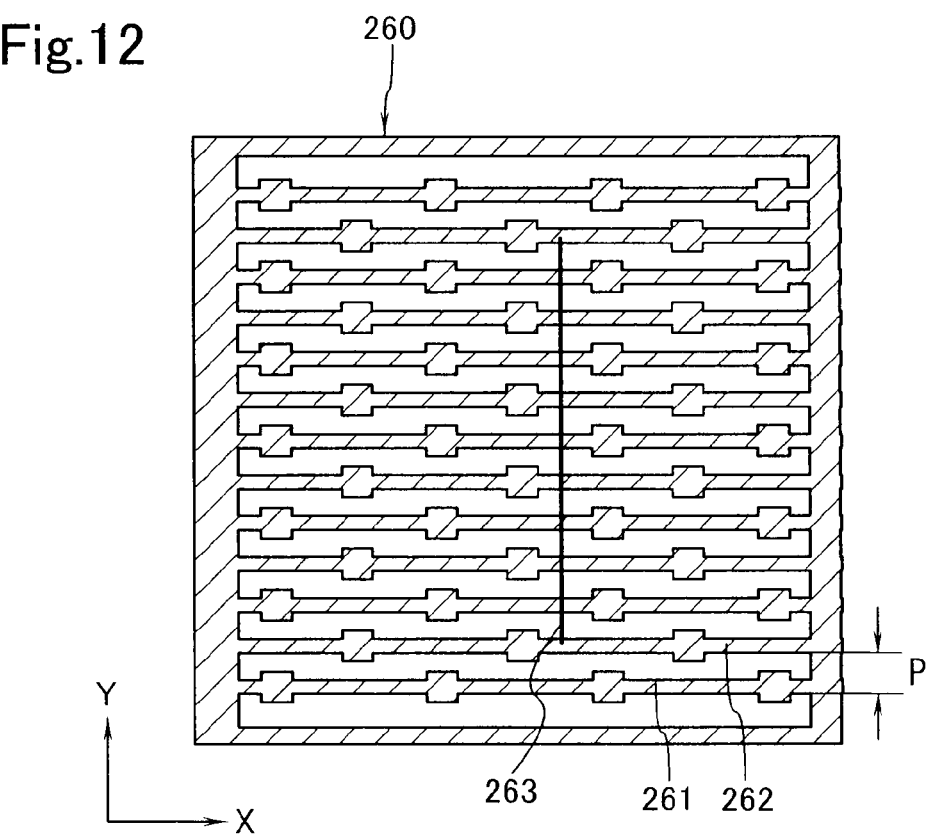
FIG. 12 is a diagram showing a pattern imaged by the TDI sensor.

A third embodiment of the present invention will next be explained with reference to FIGS. 12 through 14. FIG. 12 is a diagram showing a pattern imaged by a TDI sensor in the third embodiment.

The pattern 260 shown in FIG. 12 includes a plurality of horizontal line patterns 261 and 262 each having a predetermined pitch P. Assuming that when such a pattern 260 is imaged, the amount of light of each pixel of the TDI sensor 11 takes gradations from 0 (black pattern) to 255 (white pattern), the amount of light at all pixels do not get smaller than 63 and do not get larger than 192. Namely, when the stage 2 is moved in the X direction (i.e., TDI sensor 1 is moved relatively in the X direction) to image the pattern 260, an arbitrary pixel of the TDI sensor 11 has a possibility of simply reaching only black patterns 261 and 262 hatched in FIG. 12 and reaching no white patterns. When attention is given to another pixel, it has a possibility of simply reaching white patterns alone and reaching no black patterns. In doing so, there is a case in which both bottom and peak values with respect to all pixels of the TDI sensor 11 cannot be stored.

Figure 13:
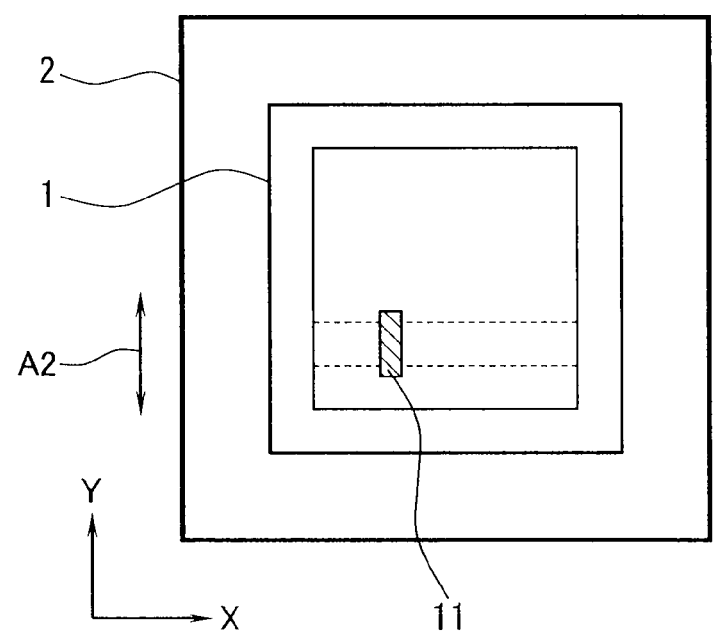
FIG. 13 is a diagram for describing a case in which a stage 2 is moved in a Y direction in a third embodiment of the present invention.
Figure 14:
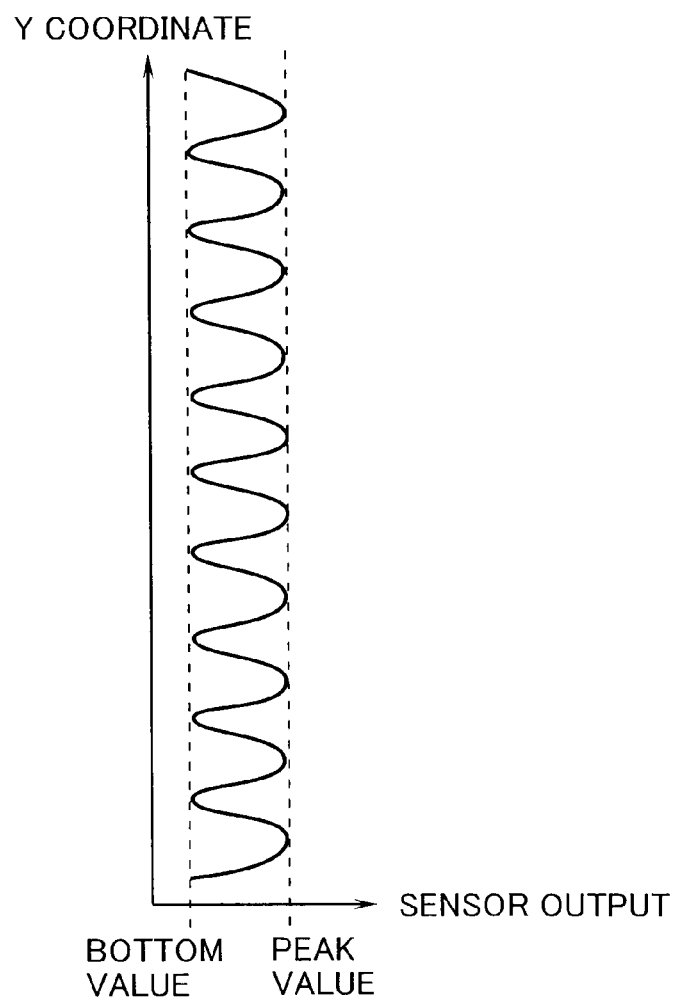
FIG. 14 is a diagram showing a TDI sensor output obtained when a linear portion 263 shown in FIG. 12 is imaged.

Thus, in the third embodiment, the stage 2 is moved in a Y direction as indicated by arrow A2 upon the relationship of position between a reticle 1 and a TDI sensor 11 such as shown in FIG. 13. When the stage 2 is moved in the Y direction in this way here to image the pattern 260, a sensor output corresponding to a straight line 263 shown in FIG. 12 becomes such a sensor output as shown in FIG. 14. The length of the straight line 263 can be set to a length equal to ten times the pattern pitch P. Consequentially, even though a sampling error of the TDI sensor 11 is taken into consideration, there can be obtained an opportunity that all the pixels of the TDI sensor 11 reach both white and black patterns. Thus, even if the pattern containing the line patterns 261 and 262 extending in the X direction of the reticle 1 is imaged as shown in FIG. 12, both bottom and peak values can be stored at each pixel.

Since, however, the TDI sensor 11 stores electrical charges therein where the TDI sensor 11 is used as an image sensor, the TDI direction is slanted (45°) when the TDI speed and the stage moving speed in the Y direction are equal to each other. Therefore, it is preferred to move the stage in the Y direction at a speed sufficiently slower than the TDI speed. For example, the stage moving speed can be set to $\frac{1}{10}$ of the TDI speed. When 2 to 3 μsec are taken to shift an electrical charge by one pixel (70 nm) in the TDI sensor 11, the speed thereof is brought to ten and a few mm/sec upon conversion into the stage moving speed. It is therefore possible to set the stage moving speed to a few mm/sec.

Incidentally, since it is not necessary to consider the storage of charges where a line sensor is used as an image sensor as an alternative to the TDI sensor, the stage moving speed corresponding to an imaging period may be set.

Figure 15:
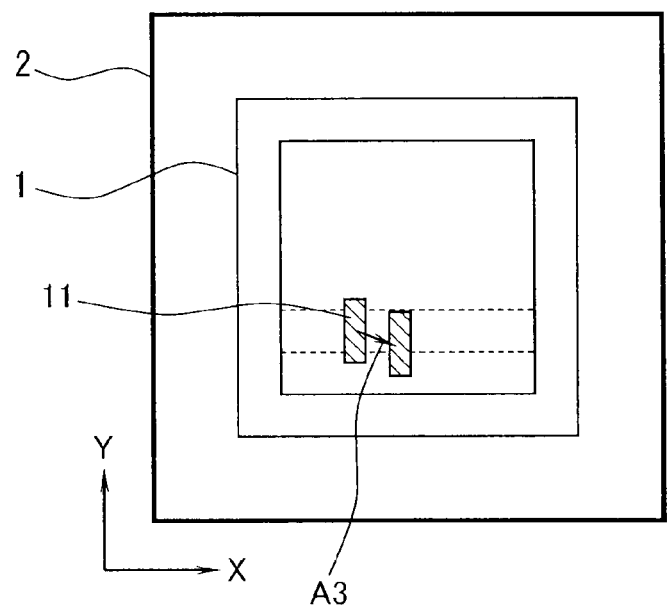
FIG. 15 is a diagram for describing a case in which the stage 2 is moved simultaneously in both X and Y directions in the third embodiment of the present invention.
Figure 16:
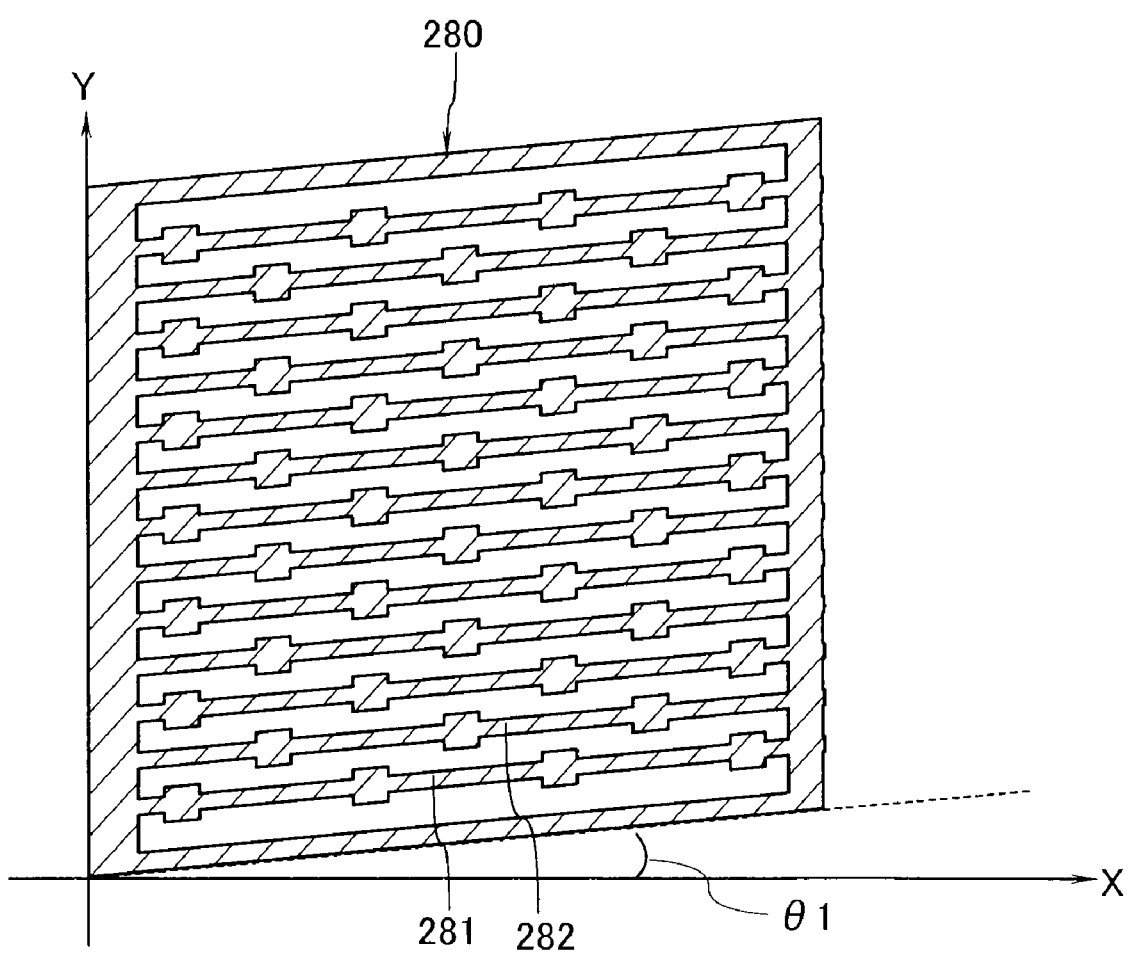
FIG. 16 is a diagram showing an image taken where the stage 2 is moved as shown in FIG. 15.

When the stage 2 is moved in an oblique direction as indicated by arrow A3, i.e., it is moved in the Y direction simultaneously with its movement in the X direction upon the relationship of position between a reticle 1 and a TDI sensor 11 such as shown in FIG. 15, an image (skew image) 280 in which patterns 281 and 282 extend in a slanting direction by an angle θ1 with respect to an X axis, is imaged as shown in FIG. 16. Even in such a case, the opportunity of allowing all pixels of the TDI sensor 11 to reach both white and black patterns can be obtained in a manner similar to the case where the stage 2 is moved in the Y direction as shown in FIG. 13. Incidentally, the moving speed of the stage 2 in the X direction is set slower than the TDI operating speed, thereby making it possible to obtain sufficient signal amplitude in a manner similar to the second embodiment.

Fourth Embodiment

A fourth embodiment of the present invention will next be explained with reference to FIGS. 17 through 20.

The first embodiment has described the calibration for the offset and gain of the sensor amplifier, which is carried out before the defect inspection.

Figure 17:
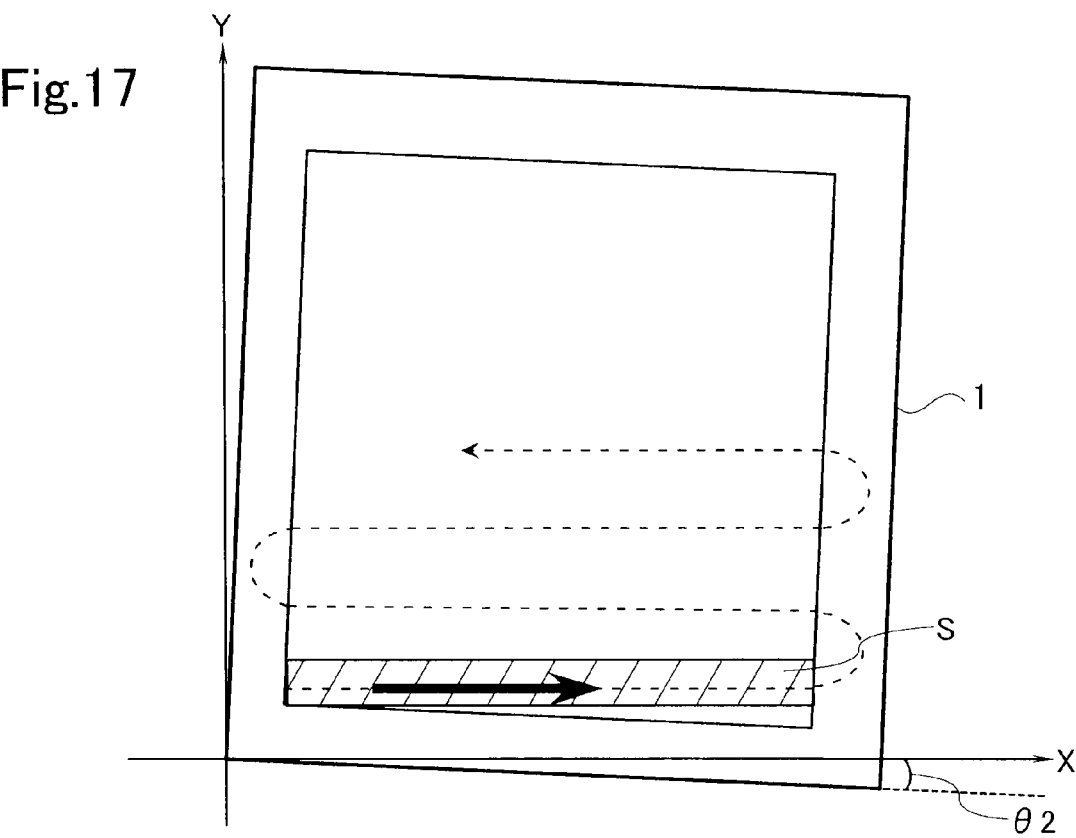
FIG. 17 is a diagram illustrating a case in which the orthogonality of a reticle 1 is insufficient with respect to a stage moving direction (X and Y directions)
Figure 18:
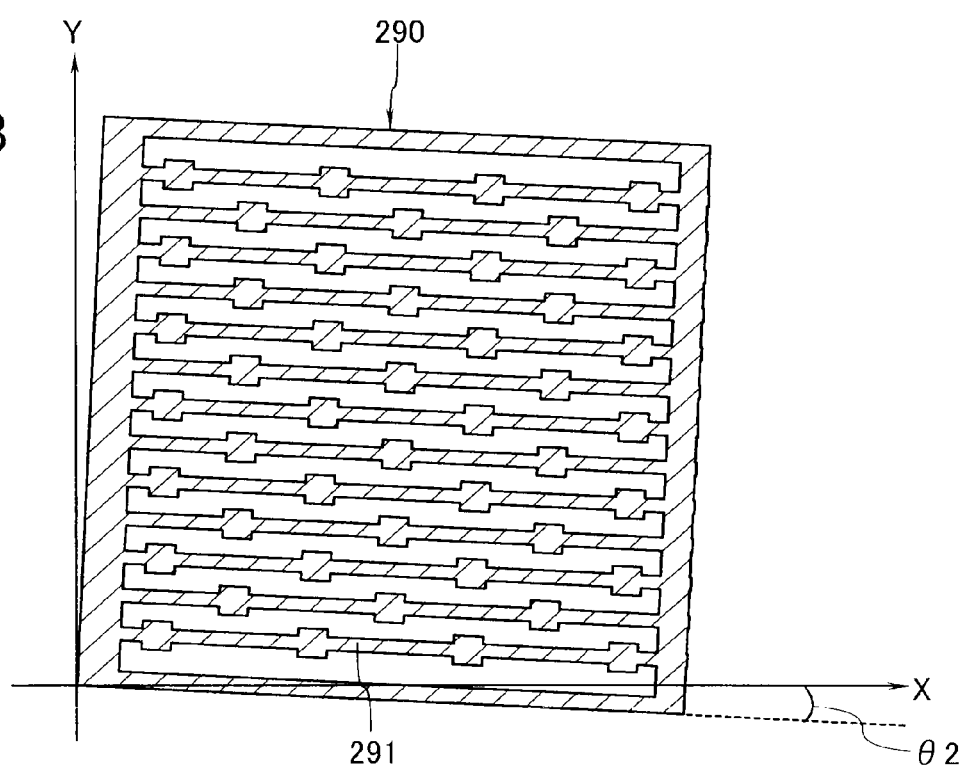
FIG. 18 is a diagram depicting an example of an image taken by a TDI sensor 11 where the orthogonality of the reticle 1 is insufficient.

Incidentally, there is a case in which the parallelism of a reticle 1 is insufficient with respect to a stage moving direction (X and Y directions) as shown in FIG. 17. In the example illustrated in FIG. 17, the reticle 1 is inclined by an angle θ2 with respect to the X direction. In this case, when a stage 2 is moved in the X direction to image a pattern by a TDI sensor 11, a pattern 290 including line patterns 291 which extends in an oblique direction by the angle θ2 with respect to the X axis is imaged as shown in FIG. 18.

Thus, in order to prevent the imaging of the pattern in such an oblique direction, stage θ-rotational alignment (called also "mask rotational alignment") is carried out before a pattern defect inspection. That is, the stage 2 is rotated by the corresponding θ-direction motor 4C before the defect inspection in such a manner that the horizontal direction of each pattern formed in the reticle 1 and the moving direction of the stage 2 become parallel.

The process of θ-rotational alignment for the conventional reticle has used a plurality of alignment marks Ma formed in a non-inspection region as shown in FIG. 4. After the coordinates (center coordinates of cross pattern, for example) of the plural alignment marks Ma have been determined, the parallelism of the reticle 1 relative to the moving direction of the stage 2 was calculated and the stage 2 was rotated based on the parallelism. Even in the case of a reticle free of the alignment marks, there has also been adopted, for example, a method for imaging an identical Y-coordinate edge pattern determined from design data in patterns of a reticle to be inspected, at a preferably spaced X-coordinate distance, determining parallelism thereof relative to a stage moving axis and performing a θ-rotational correction thereon.

However, the method using each pattern of the reticle to be inspected needs the work of performing imaging by manipulating the inspection apparatus and repeating a θ-rotation correcting operation thereby to make convergence to within a predetermined allowable rotational error. In this method, an operator needs to specify an edge pattern manually. Therefore, there were a possibility of throughput of the apparatus being degraded and a possibility of the accuracy of the stage θ-rotational alignment being reduced under the influence of pattern specified accuracy by the operator.

Therefore, the fourth embodiment will explain a stage alignment method using a product reticle formed with no alignment marks Ma. FIGS. 19 through 22 are respectively diagrams for describing the stage alignment method according to the fourth embodiment.

Figure 19:
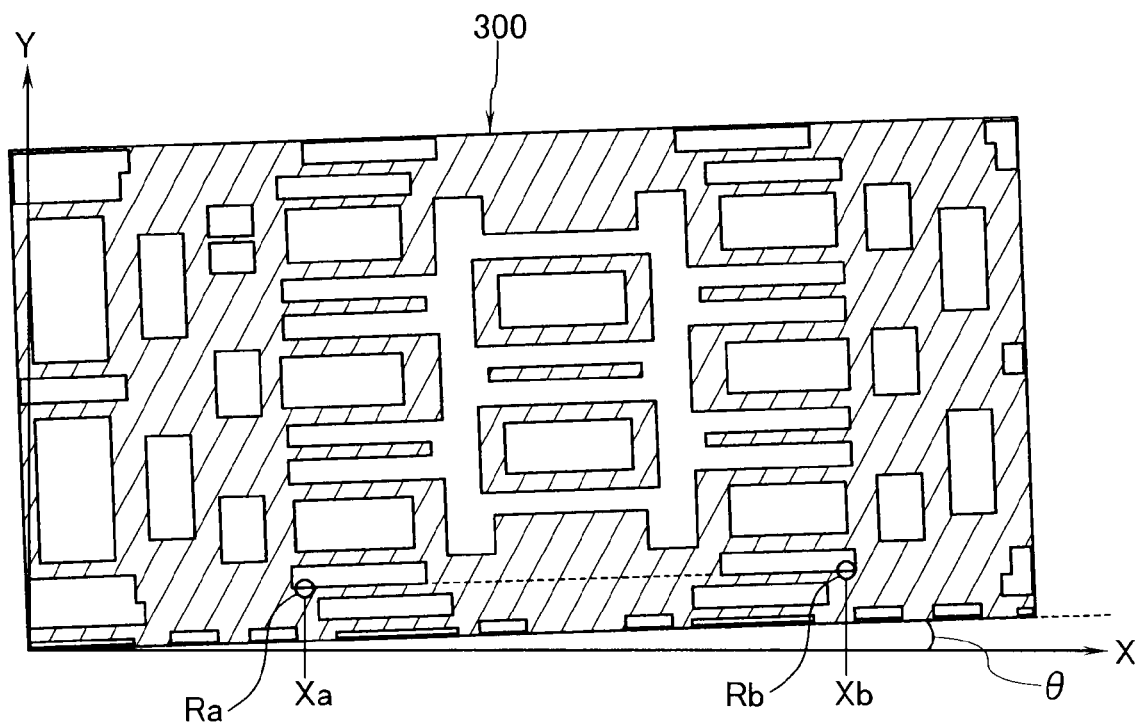
FIG. 19 is a diagram illustrating an example of each pattern searched when a stage alignment method according to a fourth embodiment of the present invention is performed.

A pattern 300 in which Y coordinates of pattern edges are identical at two X coordinates Xa and Xb as shown in FIG. 19 is first searched. Attention is paid to a change in amount-of-light P at each of regions Ra and Rb in the neighborhood of the pattern edges. The regions Ra and Rb are respectively imaged by a plurality of pixels (four pixels, for example) continued in a Y direction.

Figure 20A:
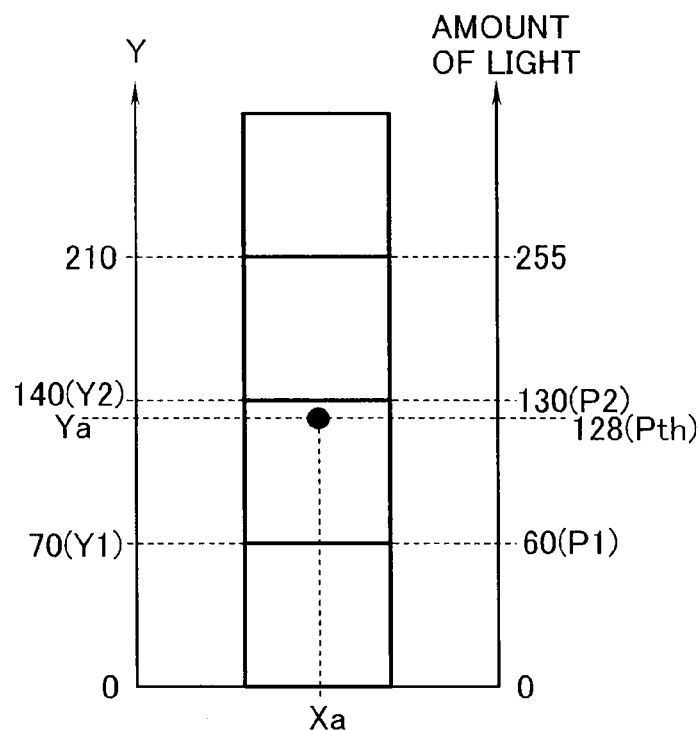
FIG. 20A is a diagram showing a pattern edge (Xa, Ya) of a region Ra shown in FIG. 19.
Figure 20B:
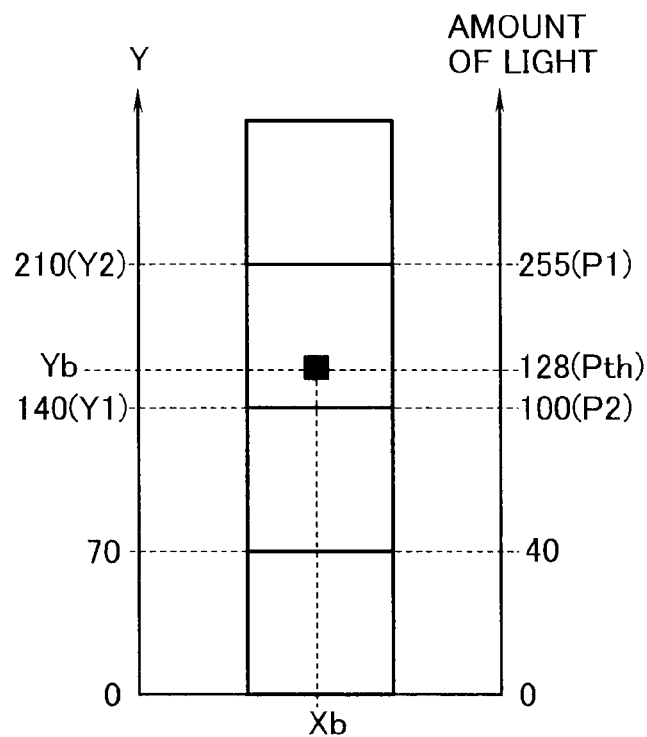
FIG. 20B is a diagram illustrating a pattern edge (Xb, Yb) of a region Rb shown in FIG. 19.

Assume now that the amount-of-light P measured at each hatched part (black pattern) shown in FIG. 19 is 0 and the amount-of-light P measured at each white part (white pattern) is 255. In doing so, an amount-of-light threshold Pth of each pattern edge corresponding to the boundary between the black and white patterns becomes 128 that lies midway therebetween. ● shown in FIG. 20A indicates a pattern edge (Xa, Ya) in the region Ra. ■ shown in FIG. 20B indicates a pattern edge (Xb, Yb) in the region Rb. In FIGS. 20A and 20B, four squares arranged in the Y direction respectively indicate four pixels of a TDI sensor. A Y coordinate at the bottom of each pixel is shown in one vertical axis. The amount-of-light at the bottom is shown in the other vertical axis. Assuming that as shown in FIGS. 20A and 20B, Y coordinates at the bottoms of two pixels with the amount-of-light Pth (=128) interpose therebetween are Y1 and Y2 (Y1<Y2) respectively, and the amount-of-light at Y1 and Y2 are P1 and P2 respectively, the Y coordinate corresponding to the amount-of-light Pth can be expressed in the weighted average like the following equation (1):

$$Y = Y1 + (Y2-Y1)/(P2-P1) \times (Pth-P1) \tag{1}$$

Then, Y coordinates Ya and Yb at which the amount-of-light P at Xa and Xb=128 are calculated with the X coordinates Xa and Xb of FIG. 19 being spaced 50 mm away from each other. Described specifically, the Y coordinate Ya is calculated as Ya=138 [nm] by substituting Y1=70, Y2=140, P1=60, P2=130 and Pth=128 shown in FIG. 20A into the equation (1). The Y coordinate Yb is calculated as Yb=152.6 [nm] by substituting Y1=140, Y2=210, P1=100, P2=255 and Pth=128 shown in FIG. 20B into the equation (1).

Figure 21:
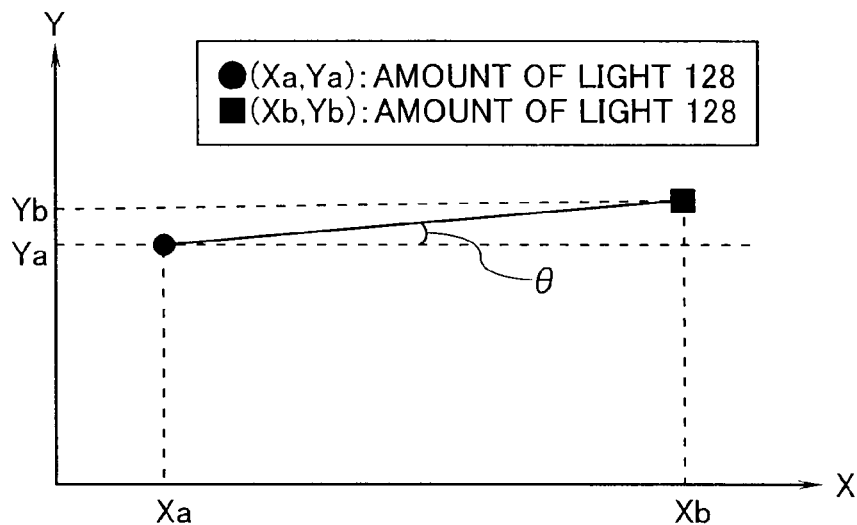
FIG. 21 is a diagram for describing a method for calculating a tilt $\theta$ of a pattern from two pattern edges.

Assuming that the tilt or slope of each pattern is θ [rad], the tilt θ is represented as the slope of a straight line that connects two edge positions (Xa, Ya) and (Xb, Yb) as shown in FIG. 21. Therefore, tan θ can be expressed like the following equation (2):

$$\tan\theta = (Yb-Ya)/(Xb-Xa) \tag{2}$$

Substituting Yb=152.6 [nm], Ya=138 [nm], Xb=75×10³ [nm] and Xa=25×10³ [nm] into the equation (2), θ is calculated as θ=2.92×10⁻⁴ [rad]. The stage 2 is rotated by the corresponding motor 4C by an angle corresponding to the calculated θ to execute the stage θ-rotational alignment.

A target value θtgt is 1×10⁻⁶ [rad], for example. After the execution of the stage θ-rotational alignment, the spots of Xa and Xb are imaged again and θ is calculated. The stage θ-rotational alignment is repeatedly executed until the calculated θ falls below the target value θtgt. Thereafter, a pattern defect inspection is executed.

Figure 22:
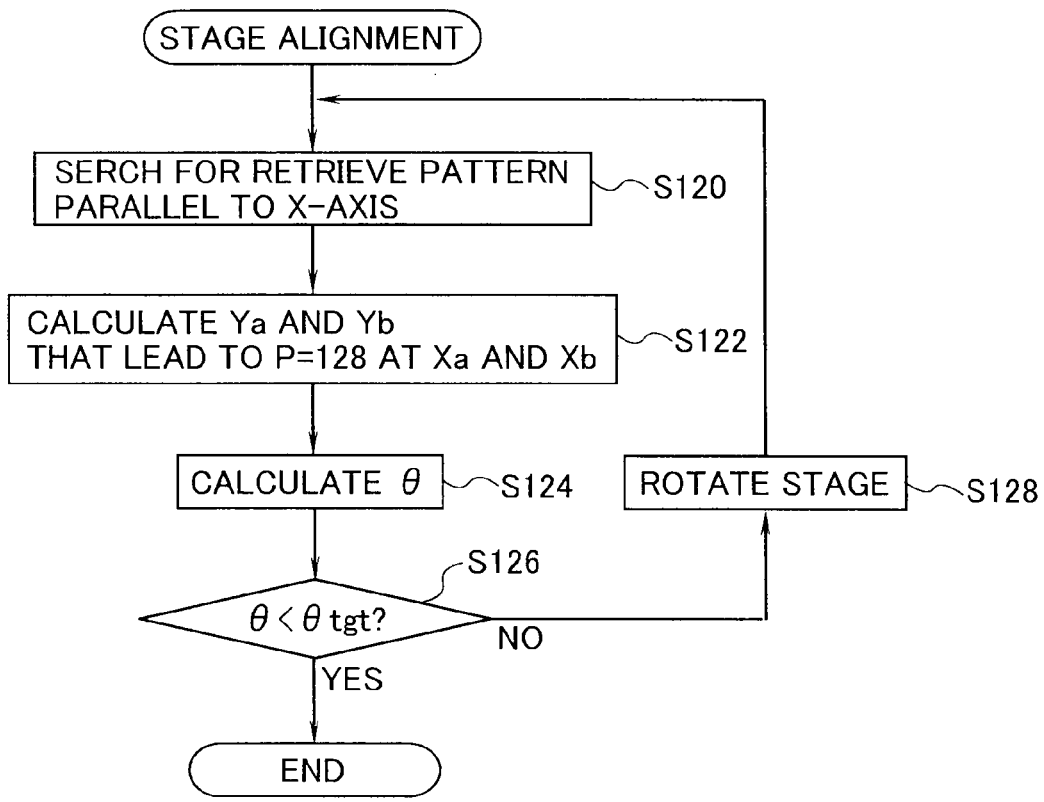
FIG. 22 is a flowchart showing a stage alignment control routine executed by a control computer 20 in the fourth embodiment of the present invention.

Specific control will be explained below with reference to FIG. 22. FIG. 22 is a flowchart showing a stage θ-rotational alignment control routine executed by the corresponding control computer 20 in the fourth embodiment. More specifically, the routine shown in FIG. 22 is started up along with the routine shown in FIG. 5 before the pattern defect inspection.

According to the routine shown in FIG. 22, patterns identical in edge position, which are spaced away from each other in parallel with the X-axis of the stage 2, are searched (Step S120). At this Step S120, for example, line patterns for power wiring, which are often formed in the neighborhood of the outer periphery of each inspection region of the reticle 1 in addition to such a pattern as shown in FIG. 19, are searched with reference to the CAD data stored in the corresponding storage device 21.

Next, Y coordinates Ya and Yb that lead to the amount-of-light P=Pth (=128) at the spaced X coordinates Xa and Xb are calculated in accordance with the equation (1) (Step S122). At this Step S122, Y coordinates at Xa=25 and Xb=75 spaced 50 mm away from each other are calculated as shown in FIG. 19, for example. Increasing the spaced width between Xa and Xb yields an increase in the difference between Ya and Yb. This is thus suitable because the accuracy of calculation of θ to be described later is achieved high. Therefore, the spaced width in the X direction may preferably be ensured as wide as possible within a range in which each suitable pattern exists. In the case of a 6-inch reticle being often distributed up to this time, the spaced width is preferably 50 mm or more, more preferably, 100 mm or more.

Next, the slope (i.e., degrees of rotational error) θ of each pattern is calculated in accordance with the equation (2) using Ya and Yb calculated at Step S124 (Step S124). It is discriminated whether the slope θ calculated at Step S124 is smaller than a target value θtgt (Step S126). This target value θtgt is $1 \times 10^{-6}$ [rad], for example. When it is discriminated at Step S126 that θ is larger than the target value θtgt, the stage 2 is rotated by the motor 4C by θ calculated at Step S124 (Step S128). Thereafter, the routine returns to the process of Step S120 and a series of processes for Steps S120, 122 and 124 referred to above are executed again.

When it is discriminated at Step S126 that θ is smaller than target value θtgt, it is determined that the stage θ-rotational alignment has been completed. In this case, the present routine is finished and the pattern defect inspection is executed.

In the fourth embodiment as described above, the plural edge positions (Xa, Ya) and (Xb, Yb) of the patterns to be made parallel to the stage moving direction are calculated in accordance with the equation (1). Thereafter, the slope θ (parallelism) of each pattern is calculated in accordance with the equation (2). The θ-rotational alignment of the stage 2 can be executed according to the calculated slope θ. Thus, the stage θ-rotational alignment can be executed using each pattern of the product reticle. Consequentially, the stage θ-rotational alignment can be executed using the product reticle formed with no alignment marks.

Further, although the Y coordinates Ya and Yb of the edge positions have been calculated as the coordinates at which the amount-of-light P of each pixel of the TDI sensor 11 is brought to the threshold value Pth (=128), this calculation can be executed simultaneously with the storage of the bottom and peak values, which has been done in each of the first through third embodiments. Thus, since the time taken for calibration prior to the defect inspection can be shortened, the throughput of the defect inspection apparatus can be enhanced.

Incidentally, in the fourth embodiment, "edge position acquiring means" according to the present invention is realized by executing the processes of Steps S120 and S122 by the control computer 20, "degrees-of-rotational error calculating means" according to the present invention is realized by executing the process of Step S124 by the control computer 20, and "alignment means" according to the present invention is realized by executing the process of Step S128 by the control computer 20, respectively. These means may be comprised of hardware respectively.

Figure 23:
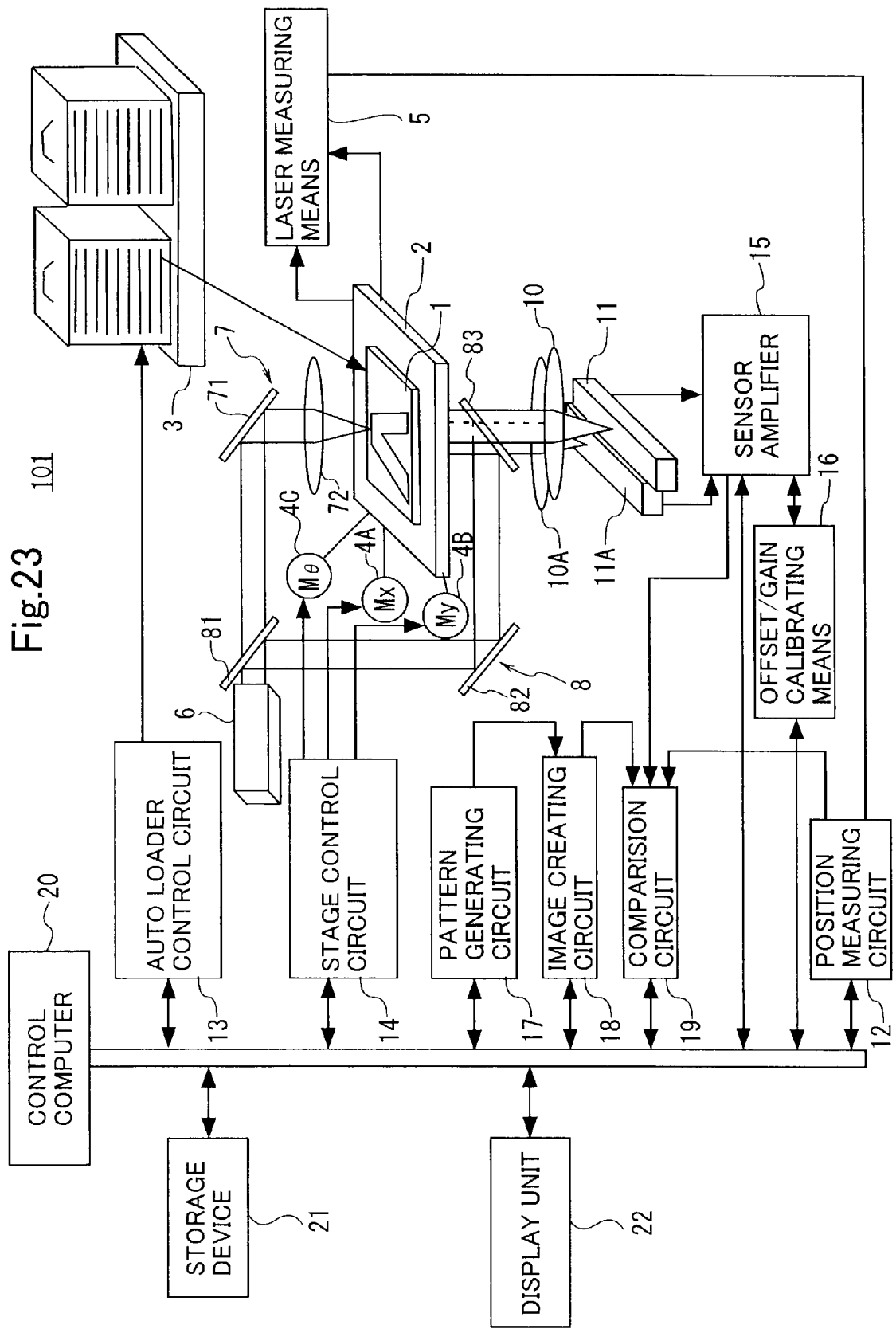
FIG. 23 is a schematic diagram illustrating a configuration of a reticle defect inspection apparatus 101 according to a modification of the present invention.

The present invention is not limited to the above embodiments, but can be modified in various ways within the scope not departing from the gist of the invention. For example, although the first embodiment has described the case where the present invention is applied to the reticle defect inspection apparatus 100 equipped with the transmission-illumination TDI sensor 11, the present invention is not limited to it, but is applicable even to a reticle defect inspection apparatus 101 further equipped with a reflection optical system 8 and a reflection illumination TDI sensor 11A as shown in FIG. 23. The reticle defect inspection apparatus 101 is further equipped with the reflection optical system 8 including a beam splitter 81, a mirror 82, a beam splitter 83 and an objective lens 10A which focuses reflected light onto the TDI sensor 11A to form an image. The calibration for the offset and gain of each pixel of the sensor amplifier 15 can be performed using the TDI sensor 11A independent of the TDI sensor 11.

Although the fourth embodiment has explained the case where the Y-coordinate identical horizontal pattern edges spaced away in the X direction are used as the patterns for the stage θ-rotational alignment, similar advantageous effects can be obtained even when the amount of rotational correction is calculated using X-coordinate identical vertical pattern edges spaced away in the Y direction on the assumption that the reticle pattern is ensured sufficiently as to its horizontal/vertical accuracy.

The features and advantages of the present invention may be summarized as follows.

In one aspect of the present invention, some of patterns are imaged by a TDI sensor prior to a defect inspection. Bottom and peak values of an amount-of-light signal of each pixel amplified by a sensor amplifier are stored. An offset of signal amplitude of each pixel of the sensor amplifier is set based on the stored bottom value of each pixel. Further, the gain of the signal amplitude of each pixel of the sensor amplifier is set based on the offset of the signal amplitude of each pixel and the stored peak value of each pixel. Thus, according to one aspect of the present invention, the offset and gain of the sensor amplifier can be set using a product reticle even though black and white regions each sufficiently wider than a TDI sensor imaging area do not exist in the product reticle.

In another aspect of the present invention, some of patterns are imaged by a TDI sensor before the inspection by detecting means. Bottom and peak values of an amount-of-light signal of each pixel amplified by a sensor amplifier are stored. An offset of signal amplitude of each pixel of the sensor amplifier is set based on the stored bottom value of each pixel. The gain of signal amplitude of each pixel of the sensor amplifier is set based on the offset of the signal amplitude of each pixel and the stored peak value of each pixel. Thus, according to another aspect of the present invention, the offset and gain of the sensor amplifier can be set using a product reticle even though black and white regions each sufficiently wider than a TDI sensor imaging area do not exist in the product reticle.

Obviously many modifications and variations of the present invention are possible in the light of the above teachings. It is therefore to be understood that within the scope of the appended claims the invention may be practiced otherwise than as specifically described.

The entire disclosure of a Japanese Patent Applications No. 2008-129163, filed on May 16, 2008 and No. 2009-19905, filed on Jan. 30, 2009 including specification, claims, drawings and summary, on which the Convention priority of the present application is based, are incorporated herein by reference in its entirety.

What is claimed is:

1. A reticle defect inspection method in which an image sensor is moved relative to a reticle, and an optical image obtained by amplifying an output of each pixel of the image sensor by a sensor amplifier is compared with a reference image defined as a standard image relative to the optical image to perform a defect inspection of the reticle,
the sensor amplifier being capable of calibrating a gain and an offset of a signal amplitude every pixel, the reticle defect inspection method comprising, before the defect inspection:
imaging some of patterns of the reticle by the image sensor, and storing bottom and peak values of an amount-of-light signal of each pixel amplified by the sensor amplifier, wherein when the bottom and peak values of each of the pixels are stored, a relative moving speed of the reticle is set slower than a pixel moving speed determined according to a pixel size and an imaging period of the image sensor;
setting a plurality of offsets in the sensor amplifier by setting each offset of a signal amplitude for each pixel of the sensor amplifier, based on the stored bottom value of each pixel; and
setting a plurality of gains in the sensor amplifier by setting each gain of a signal amplitude for each pixel of the sensor amplifier, based on the offset of the signal amplitude of each pixel and on the stored peak value of each pixel.

2. A reticle defect inspection method in which an image sensor is moved relative to a reticle, and an optical image obtained by amplifying an output of each pixel of the image sensor by a sensor amplifier is compared with a reference image defined as a standard image relative to the optical image to perform a defect inspection of the reticle, wherein the image sensor is a TDI sensor having a plurality of stages of lines,
the sensor amplifier being capable of calibrating a gain and an offset of a signal amplitude every pixel, the reticle defect inspection method comprising, before the defect inspection:
imaging some of patterns of the reticle by the image sensor, and storing bottom and peak values of an amount-of-light signal of each pixel amplified by the sensor amplifier, wherein when the bottom and peak values of each of the pixels are stored, the relative moving speed of the reticle is set slower than a TDI operating speed of the TDI sensor;
setting a plurality of offsets in the sensor amplifier by setting each offset of a signal amplitude for each pixel of the sensor amplifier, based on the stored bottom value of each pixel; and
setting a plurality of gains in the sensor amplifier by setting each gain of a signal amplitude for each pixel of the sensor amplifier, based on the offset of the signal amplitude of each pixel and on the stored peak value of each pixel.

3. A reticle defect inspection method in which an image sensor is moved relative to a reticle, and an optical image obtained by amplifying an output of each pixel of the image sensor by a sensor amplifier is compared with a reference image defined as a standard image relative to the optical image to perform a defect inspection of the reticle,
the sensor amplifier being capable of calibrating a gain and an offset of a signal amplitude every pixel, the reticle defect inspection method comprising, before the defect inspection:
imaging some of patterns of the reticle by the image sensor, and storing bottom and peak values of an amount-of-light signal of each pixel amplified by the sensor amplifier;
setting a plurality of offsets in the sensor amplifier by setting each offset of a signal amplitude for each pixel of the sensor amplifier, based on the stored bottom value of each pixel; and
setting a plurality of gains in the sensor amplifier by setting each gain of a signal amplitude for each pixel of the sensor amplifier, based on the offset of the signal amplitude of each pixel and on the stored peak value of each pixel;
acquiring edge positions at plural spots of reticle patterns each approximately parallel to a relative moving direction of the image sensor upon storing the bottom and peak values of the respective pixels;
calculating degrees of rotational error of the reticle from acquired edge positions; and
executing a rotational alignment of the reticle, based on the calculated degrees of rotational error.

4. The reticle defect inspection method according to claim 3 wherein, in the acquiring the edge positions, amount-of-light and coordinates of the pixels, which are obtained by imaging the neighborhood of the edge positions, are acquired, and edge positions each brought to a predetermined amount-of-light are calculated, based on the acquired amount-of-light and coordinates of the pixels.

5. A reticle defect inspection method in which an image sensor is moved relative to a reticle, and an optical image obtained by amplifying an output of each pixel of the image sensor, wherein the image sensor is a TDI sensor having a plurality of stages of lines, by a sensor amplifier is compared with a reference image defined as a standard image relative to the optical image to perform a defect inspection of the reticle,
the sensor amplifier being capable of calibrating a gain and an offset of a signal amplitude every pixel, the reticle defect inspection method comprising, before the defect inspection:
imaging some of patterns of the reticle by the image sensor, and storing bottom and peak values of an amount-of-light signal of each pixel amplified by the sensor amplifier, wherein when some of the patterns of the reticle are imaged by the TDI sensor while the stage with the reticle placed thereon is being moved in one direction, imaging is done by the image sensor while the stage is being moved in the other direction orthogonal to the one direction where each arbitrary pixel of the TDI sensor do not reach both light-shielding and light-transmitted portions of the reticle;
setting a plurality of offsets in the sensor amplifier by setting each offset of a signal amplitude for each pixel of the sensor amplifier, based on the stored bottom value of each pixel; and
setting a plurality of gains in the sensor amplifier by setting each gain of a signal amplitude for each pixel of the sensor amplifier, based on the offset of the signal amplitude of each pixel and on the stored peak value of each pixel;
wherein a stage moving speed in the other direction is set slower than a TDI operating speed of the TDI sensor.

6. A reticle defect inspection apparatus comprising:
- a light irradiating mechanism for irradiating a reticle formed with each pattern with light;
- a driving unit for driving a stage which holds the reticle thereon;
- an image sensor for detecting an amount-of-light signal of light transmitted through or reflected from the reticle at a plurality of pixels;
- a sensor amplifier for amplifying an output of each pixel of the image sensor every pixel and generating an optical image, the sensor amplifier being capable of calibrating a gain and an offset of a signal amplitude every pixel;
- a reference image generating unit for generating a reference image defined as a standard image relative to the optical image;
- a detecting unit for comparing the optical image with the reference image thereby to detect a defect of each pattern of the reticle;
- a storing unit, when the stage is driven by the driving unit before the inspection by the detecting unit to image some of the patterns by the image sensor, for storing bottom and peak values of an amount-of-light signal of each pixel amplified by the sensor amplifier, wherein a stage moving speed at the time that the bottom and peak values are stored by the storing unit, is set slower than a pixel moving speed determined according to a pixel size and an imaging period of the image sensor;
- an offset setting unit for setting an offset of a signal amplitude for each pixel of the sensor amplifier, based on the bottom value of each pixel stored by the storing unit; and
- a gain setting unit for setting a gain of a signal amplitude for each pixel of the sensor amplifier, based on the offset of the signal amplitude for each pixel and the peak value of each pixel stored by the storing unit.

7. A reticle defect inspection apparatus comprising:
- a light irradiating mechanism for irradiating a reticle formed with each pattern with light;
- a driving unit for driving a stage which holds the reticle thereon;
- an image sensor for detecting an amount-of-light signal of light transmitted through or reflected from the reticle at a plurality of pixels, wherein the image sensor is a TDI sensor that stores the amount-of-light signal on each of a plurality of stages of lines;
- a sensor amplifier for amplifying an output of each pixel of the image sensor every pixel and generating an optical image, the sensor amplifier being capable of calibrating a gain and an offset of a signal amplitude every pixel;
- a reference image generating unit for generating a reference image defined as a standard image relative to the optical image;
- a detecting unit for comparing the optical image with the reference image thereby to detect a defect of each pattern of the reticle;
- a storing unit, when the stage is driven by the driving unit before the inspection by the detecting unit to image some of the patterns by the image sensor, for storing bottom and peak values of an amount-of-light signal of each pixel amplified by the sensor amplifier, wherein a stage moving speed at the time that the bottom and peak values are stored by the storing unit is set slower than a TDI operating speed of the TDI sensor;
- an offset setting unit for setting an offset of a signal amplitude for each pixel of the sensor amplifier, based on the bottom value of each pixel stored by the storing unit; and
- a gain setting unit for setting a gain of a signal amplitude for each pixel of the sensor amplifier, based on the offset of the signal amplitude for each pixel and the peak value of each pixel stored by the storing unit.

8. A reticle defect inspection apparatus comprising:
- a light irradiating mechanism for irradiating a reticle formed with each pattern with light;
- a driving unit for driving a stage which holds the reticle thereon;
- an image sensor for detecting an amount-of-light signal of light transmitted through or reflected from the reticle at a plurality of pixels;
- a sensor amplifier for amplifying an output of each pixel of the image sensor every pixel and generating an optical image, the sensor amplifier being capable of calibrating a gain and an offset of a signal amplitude every pixel;
- a reference image generating unit for generating a reference image defined as a standard image relative to the optical image;
- a detecting unit for comparing the optical image with the reference image thereby to detect a defect of each pattern of the reticle;
- a storing unit, when the stage is driven by the driving unit before the inspection by the detecting unit to image some of the patterns by the image sensor, for storing bottom and peak values of an amount-of-light signal of each pixel amplified by the sensor amplifier;
- an offset setting unit for setting an offset of a signal amplitude for each pixel of the sensor amplifier, based on the bottom value of each pixel stored by the storing unit; and
- a gain setting unit for setting a gain of a signal amplitude for each pixel of the sensor amplifier, based on the offset of the signal amplitude for each pixel and the peak value of each pixel stored by the storing unit;
- an edge position acquiring unit for acquiring edge positions at plural spots of reticle patterns each approximately parallel to a relative moving direction of the image sensor,
- a degrees-of-rotational error calculating unit for calculating degrees of rotational error of the reticle from the edge positions acquired by the edge position acquiring unit, and
- an alignment unit for executing a rotational alignment of the reticle, based on the degrees of rotational error calculated by the degrees-of-rotational error calculating unit.

9. The reticle defect inspection method according to claim 8, wherein the edge position acquiring unit calculates edge positions each brought to a predetermined amount-of-light, based on amounts of light and coordinates of the pixels, which are obtained by imaging the neighborhood of the edge positions.

* * * * *